(12) United States Patent
Toreki et al.

(10) Patent No.: US 9,549,547 B2
(45) Date of Patent: Jan. 24, 2017

(54) REGENERATION OF ANTIMICROBIAL COATINGS CONTAINING METAL DERIVATIVES UPON EXPOSURE TO AQUEOUS HYDROGEN PEROXIDE

(71) Applicant: Quick-Med Technologies, Inc., Gainesville, FL (US)

(72) Inventors: William Toreki, Gainesville, FL (US); Rustom S. Kanga, Kennesaw, GA (US)

(73) Assignee: QUICK-MED TECHNOLOGIES INC., Gainesville, FL (US)

( * ) Notice: Subject to any disclaimer, the term of this patent is extended or adjusted under 35 U.S.C. 154(b) by 0 days.

(21) Appl. No.: 14/396,033

(22) PCT Filed: Dec. 21, 2013

(86) PCT No.: PCT/US2013/077333
§ 371 (c)(1),
(2) Date: Oct. 21, 2014

(87) PCT Pub. No.: WO2014/100778
PCT Pub. Date: Jun. 26, 2014

(65) Prior Publication Data
US 2016/0037766 A1    Feb. 11, 2016

Related U.S. Application Data

(60) Provisional application No. 61/740,075, filed on Dec. 20, 2012.

(51) Int. Cl.
| | |
|---|---|
| *A01N 59/00* | (2006.01) |
| *B05D 3/00* | (2006.01) |
| *A01N 25/10* | (2006.01) |
| *A61L 2/00* | (2006.01) |
| *A61L 9/00* | (2006.01) |
| *A01N 59/16* | (2006.01) |
| *A61L 27/44* | (2006.01) |
| *A61L 27/56* | (2006.01) |
| *A61L 28/00* | (2006.01) |
| *A61L 29/12* | (2006.01) |
| *A61L 29/14* | (2006.01) |
| *A61L 31/12* | (2006.01) |
| *A61L 31/14* | (2006.01) |
| *A61L 2/20* | (2006.01) |
| *A61L 2/232* | (2006.01) |
| *A61L 2/238* | (2006.01) |
| *C09D 5/14* | (2006.01) |
| *C09D 7/12* | (2006.01) |
| *C09D 11/00* | (2014.01) |
| *C08K 3/22* | (2006.01) |

(52) U.S. Cl.
CPC .............. *A01N 25/10* (2013.01); *A01N 59/00* (2013.01); *A01N 59/16* (2013.01); *A61L 2/00* (2013.01); *A61L 2/208* (2013.01); *A61L 2/232* (2013.01); *A61L 2/238* (2013.01); *A61L 9/00* (2013.01); *A61L 27/446* (2013.01); *A61L 27/56* (2013.01); *A61L 28/0092* (2013.01); *A61L 29/126* (2013.01); *A61L 29/146* (2013.01); *A61L 31/128* (2013.01); *A61L 31/146* (2013.01); *C09D 5/14* (2013.01); *C09D 7/1225* (2013.01); *C09D 7/1266* (2013.01); *A61L 2202/24* (2013.01); *A61L 2420/04* (2013.01); *C08K 2003/2217* (2013.01); *C08K 2003/2237* (2013.01); *C08K 2003/2244* (2013.01); *C08K 2003/2296* (2013.01); *C09D 11/00* (2013.01)

(58) Field of Classification Search
CPC ............ A01N 59/16; A61L 15/44; B05D 3/00
USPC .................................... 424/618; 427/337, 2.1
See application file for complete search history.

(56) References Cited

U.S. PATENT DOCUMENTS

| | | | |
|---|---|---|---|
| 740,832 A | 10/1903 | Elias | |
| 2,563,442 A | 8/1951 | Wood et al. | |
| 4,172,841 A | 10/1979 | Danna et al. | |
| 4,174,418 A | 11/1979 | Welch et al. | |
| 5,656,037 A | 8/1997 | Vigo et al. | |
| 8,124,169 B2 * | 2/2012 | Ylitalo | A01N 25/10 427/8 |
| 2002/0185199 A1 | 12/2002 | Myers et al. | |
| 2007/0243237 A1 * | 10/2007 | Khaled | A01N 25/10 424/443 |
| 2010/0247615 A1 * | 9/2010 | Toreki | A61L 15/60 424/447 |
| 2011/0171280 A1 * | 7/2011 | Toreki | D06M 11/155 424/411 |
| 2011/0206578 A1 | 8/2011 | Foster et al. | |
| 2013/0183495 A1 * | 7/2013 | Rock | D06M 11/50 428/156 |

FOREIGN PATENT DOCUMENTS

WO        2009018009 A1    2/2009

OTHER PUBLICATIONS

Xie, Yanping; He, Yiping; Irwin, Peter L.; Jin, Tony; and Shi, Xianming; "Antimicrobial Activity and Mechanism of Action of Zinc Oxide Nanoparticles Against Camylobacter jejuni", Applied and Environmental Microbiology 77(7), p. 2325-2331, (2011).

(Continued)

*Primary Examiner* — Cachet Sellman
(74) *Attorney, Agent, or Firm* — Gerry J. Elman; Elman Technology Law, P.C.

(57) ABSTRACT

This invention relates to regenerable antimicrobial coatings with long-lasting efficacy for use in medical applications including implants, medical instruments or devices, and hospital equipment. The same coatings would also have broad utility in the consumer, industrial, and institutional markets. The coating technology would be based on sequestration of hydrogen peroxide (HP) by zinc oxide binders incorporated into the coatings.

23 Claims, No Drawings

(56) References Cited

OTHER PUBLICATIONS

Yousef, Jehad M.; and Danial, Enas N.; "In Vitro Antibacterial Activity and Minimum Inhibitory Concentration of Zinc Oxide and Nano-particle Zinc Oxide Against Pathogenic Strains", Journal of Health Sciences 2(4), p. 38-42, (2012).

Wang, Chao; Liu, Lian-Long; Zhang, Ai-Ting; Xie, Peng; Lu, Jian-Jun; and Zou, Ziao-Ting; "Antimicrobial Effects of Zinc Oxide Nanoparticles on *Escherichia coli* K88", African Journal of Biotechnology 11(44), p. 10248-10254, (2012).

Sevinc, Berdan, Aydin, and Hanley, Luke; "Antimicrobial Activity of Dental Composites Containing Zinc Oxide Nanoparticles", Journal of Biomedical Materials Research, Part B, Applied Biomaterials 94(1), p. 22-31 (2011).

Seil, Justin T.; and Webster, Thomas J.; "Zinc Oxide Nanoparticle and Polymer Antimicrobial Biomaterial Composites", MRS Proceedings 1316, (2010) [Abstract].

Chang, B. P.; Akil, H. Md.; Nasir, R. Md.; and Nurdijati, S.; "Mechanical and Antimicrobial Properties of Treated and Untreated Zinc Oxide Filled UHMWPE Composites", Journal of Thermoplastic Composite Materials 24(5), p. 653-667, (2011) [Abstract].

Singh, Gagandeep; Joyce, Eadaoin M.; Beddow, James; and Mason, Timothy J.; "Evaluation of Antimicrobial Activity of ZnO Nanoparticles Coated Sonochemically onto Textile Fabrics", Biotechnology and Food Sciences 2(1), p. 106-120, (2012).

Rajendran, R.; Balakumar, C.; Ahammed, Hasabo A.; Mohammed, Jayakumar S.; Vaideki, K.; and Rajesh, E.M.; "Use of Zinc Oxide Nano Particles for Production of Antimicrobial Textiles", International Journal of Engineering, Science and Technology 2(1), p. 202-208, (2010).

Gittard, Shaun D.; Perfect, John R.; Montiero-Riviere, Nancy A; Wei, Wei; Jin, Chunming; and Narayan, Robert, J.; "Assessing the Antimicrobial Activity of Zinc Oxide Thin Films Using Disk Diffusion and Biofilm Reactor", Applied Surface Science 255(11), p. 5806-5811, (2009) [Abstract].

Zhang, Lingling; Jiang, Yunhong; Ding, Yulong; Daskalakis, Nikolaos; Jeuken, Lars; Povey, Malcolm; O'Neill, Alex J.; and York, David W.; "Mechanistic Investigation into Antimicrobial Behavior of Suspensions of ZnO Nanoparticles against *E. coli*", Journal of Nanoparticle Research 12(5), p. 1625-1636, (2010).

Rosenthal-Toib, Liora; Zohar, Keren; Alagem, Meital; and Tsur, Yoed; "Synthesis of Stabilized Nanoparticles of Zinc Peroxide", Chemical Engineering Journal 136, p. 425-429, (2008, Singh, Nahar; Mittal, Shelly; Sood, K.N.; Rashmi; and Gupta, Prabat K.; "Controlling the Flow of Nascent Oxygen Using Hydrogen Peroxide Results in Controlling the Synthesis of $ZnO/ZnO_2$", Chalcogenide Letters 7(4), p. 275-281, (2010) [Abstract].

\* cited by examiner

REGENERATION OF ANTIMICROBIAL COATINGS CONTAINING METAL DERIVATIVES UPON EXPOSURE TO AQUEOUS HYDROGEN PEROXIDE

CROSS-REFERENCE TO RELATED APPLICATIONS

This application is a national stage entry of International Patent Application, Ser. No PCT/US2013/077333, filed Dec. 21, 2013, which claims benefit of priority to U.S. Provisional Patent Application 61/740,075 filed Dec. 20, 2012. The entire disclosures of each of the aforementioned applications are incorporated herein by reference.

TECHNICAL FIELD

This invention pertains to regenerable coatings with durable antimicrobial properties.

BACKGROUND ART

Healthcare facilities are known to be a breeding ground for a variety of infectious diseases. The pathogens that cause these diseases can reside in many places in the hospital environment—not just in devices and equipment used in medical procedures, but also from common surfaces such as floors, telephones, bed rails, bathroom fixtures, hand rails, and computer keyboards. Microbes living on these contaminated surfaces are touched by multiple people leading to increased spread of hospital acquired infections (HAIs), and it has been estimated that 1 in 20 hospital patients will be infected with an HAI as a direct result of the care they receive at hospital.

Hydrogen peroxide (HP) is currently receiving renewed attention as a safe, environmentally-friendly, and cost-effective antimicrobial, as evidenced by the recent introduction of several commercially-available cleaning products based on HP.

Casual contact with everyday objects is a leading cause for the spread of infection, and disease. One dirty hand can infect multiple surfaces. Rubbing one's eye or eating a sandwich then becomes a vector for infection. Even surfaces are cleaned and sanitized frequently can quickly become recontaminated after the applied disinfectant has evaporated.

Antimicrobial cleaning products based on hydrogen peroxide have recently been commercialized for hospital and home use by several leading brands, including Clorox and Lysol. Unfortunately, since HP is volatile, surfaces cleaned with these products (or even with alcohol, bleach, etc.) lose the antimicrobial effect immediately after drying.

Hospitals, nursing homes, and other healthcare facilities are known to be a breeding ground for a variety of infectious diseases. The pathogens that cause these diseases can reside in many places in the hospital environment including floors, curtains, telephones, bedding, bed rails, chairs and chair backs, hand rails, and computer keyboards. In a surface contamination targeting study conducted in a Welsh hospital, 2,573 touch actions were examined The results showed that 1,489 touch actions were by nurses, 519 were by patients, 380 were by visitors, and 185 were by physicians (Obee, Peter; PhD Thesis: "Hospital Surfaces and their Importance in Cross Contamination and the Spread and Transmission of Bacteria", Accessed: University of Wales, Institute Cardiff Repository URI: <http://hdl.handle.net/10369/844>). This demonstrates the high potential for spreading of microbes from one group to the other. In an extensive contamination study based in a southern Ontario hospital, 11.8% of surfaces sampled were positive for MRSA (n=612) while 2.4 (n=552) of surfaces were positive for *C. difficile* (Faires, Meredith C.; Pearl, David L.; Ciccotelli, William A.; Straus, Karen; Zinken, Giovanna; Berke, Olaf; Reid-Smith, Richard J.; and Weese, J. Scott; "A Prospective Study to Examine the Epidemiology of Methicillin-Resistant *Staphylococcus aureus* and *Clostridium difficile* Contamination in the General Environment of Three Community Hospitals in Southern Ontario, Canada", BMC Infectious Diseases 12(290), (2012). Furthermore, a study from as far back as 1997 discovered that 42% of medical personnel who had no direct contact with actual infected patients, had MRSA contaminated gloves acquired directly from hospital room surfaces (Boyce, John M.; Potter-Bynoe, Gail; Chenevert, Claire; and King, Thomas; "Environmental Contamination Due to Methicillin-Resistant *Staphylococcus aureus*: Possible Infection Control Implications", Infection Control and Hospital Epidemiology 18(9), p 622-627, (1997). Other studies indicated that certain Gram-positive species such as *Staph. aureus* can survive up to 7 months on dry surfaces, while certain Gram-negative organisms such as *E. coli* and *Pseudomonas aeruginosa* can last up to 16 months on dry surfaces (Kramer, Axel; Schwebke, Ingeborg; and Kampf, Günter: "How Long Do Nosocomial Pathogens Persist on inanimate Surfaces? A Systematic Review", BMC Infectious Diseases 6(1), p 130, (2006).

Contaminated surfaces such as these are leading to increased incidences of hospital acquired infections (HAIs) and it has been estimated that 1 in 20 hospital patients will be infected with an HAI as a direct result of the care they receive at hospital institutions (Scott II, R. Douglas; "The Direct Costs of Healthcare-Associated Infections in U.S. Hospitals and the Benefits of Prevention", Division of Healthcare Quality Promotion: National Center for Preparedness, Detection, and Control of Infectious Diseases, Centers for Disease Control and Prevention, (2009). One study estimates that 1.7 million HAIs occurred in U.S. hospitals in 2002, leading to approximately 99,000 deaths, exceeding the number of cases of any currently notifiable disease, and also exceeding the number attributable to several of the top ten leading causes of death reported in U.S. vital statistics (Klevens, R. Monina; Edwards, Johnathan R.; Richards Jr., Chesley L.; Horan, Teresa C.; Gaynes, Robert P.; Pollock, Daniel A.; Cardo, Denise M.; "Estimating Health Care-Associated Infections and Deaths in U.S. Hospitals, 2002", Public Health Reports 1 22(2), p 160-166, (2007). Not only are these increased numbers of infections contributing to the decline of the health of U.S. citizens; the direct costs of these HAIs to hospitals are estimated to be between $28.4 and $45 billion per year in the U.S. (Scott 2009). These increased costs result from longer hospitalizations, increased use of diagnostic imaging, increased use of intensive care, and increased use of newer more expensive antibiotics. Assuming a 20%-70% HAI prevention range, preventing HAIs can have cost benefits from $5.7 billion to $31.5 billion.

Further compounding the issue, new legislation and national government programs are making serious adjustments in response to the increase of HAIs. In 2008, the United States Centers for Medicare and Medicaid Services halted reimbursements to hospitals for certain "reasonably preventable" HAIs as a result of the 2005 Deficit Reduction Act (Graves, Nicholas; and McGowan, John E.; "Nosocomial Infection, the Deficit Reduction Act, and Incentives for Hospitals", JAMA: The Journal of the American Medical Association, 300(13) p 1577-1579, (2008). Starting Jul. 1, 2012, states were required to implement non-payment polices for healthcare-associated conditions and public reporting of these infections is now mandatory. Additionally, as of Oct. 1, 2012, hospitals with HAI-associated readmission rates surpassing the predicted level will be punished with a 1% decrease of all Medicare payments and the penalty will rise to 3% by 2015 (UMF Corporation, "Doing Everything: Multimodal Intervention to Prevent Healthcare-Associated Infections", White Paper: UMF Corporation, (2012).

Hydrogen peroxide is a favored antimicrobial in many applications because its breakdown products, water and oxygen, are innocuous, and it tends to have broad spectrum antimicrobial activity, meaning that it is not only effective against bacteria, but it also kills viral and fungal organisms. Broad spectrum activity is important in situations where harmful organisms are present but their identity is not known. Hydrogen peroxide is a well-known antiseptic which has been extensively employed in aqueous solution for the treatment of infectious processes in both human and veterinary topical therapy. Both HP and zinc oxide (ZnO) have received GRAS (Generally Recognized as Safe) designations from the U.S. Food and Drug Administration (FDA). Both are also widely-available and relatively-inexpensive commodity materials.

The designation of compounds, formulations and devices as "antimicrobial" is often misused. To a layman, a 90% reduction of bacteria on a surface may seem great; however, one must remember that bacteria multiply exponentially and quickly. For instance, it is said that a single *E. coli* (EC) cell under favorable conditions can multiply into over ten million cells within 12 hours! Thus, it is imperative that a useful antimicrobial product give an extremely high level of microbial kill. For this reason, the efficacy of antimicrobial products is commonly described in terms of "log reduction." This means that a 90% kill equals 1-log reduction, and 99% kill equals a 2-log reduction. Killing 99.9999% of the bacteria equals a 6-log reduction. Regulatory agencies such as the FDA and U.S. Environmental Protection Agency (EPA) historically have required a minimum of 3-log performance for a product to be classified as "antimicrobial"; however, today a 4-log to 6-log requirement is becoming more common. For this reason, testing of bactericidal activity is commonly done using challenge levels of at least $10^6$ cfu/mL (colony forming units per milliliter).

Zinc oxide (ZnO) has received much attention in recent years as an antimicrobial agent. It has been found that ZnO nanoparticles show a higher efficacy than conventional ZnO powders in the micron size range. This is to be expected, based on the higher surface area of the nanoparticles. Indeed, high antimicrobial efficacy is realized for ZnO nanoparticles in suspension (i.e. as liquid antimicrobial products) for various pathogenic bacteria [Xie, Yanping; He, Yiping; Irwin, Peter L.; Jin, Tony; and Shi, Xianming; "Antimicrobial Activity and Mechanism of Action of Zinc Oxide Nanoparticles Against Camylobacter jejuni", *Applied and Environmental Microbiology* 77(7), p 2325-2331, (2011); Yousef, Jehad M.; and Danial, Enas N.; "In Vitro Antibacterial Activity and Minimum Inhibitory Concentration of Zinc Oxide and Nano-particle Zinc Oxide Against Pathogenic Strains", *Journal of Health Sciences* 2(4), p 38-42, (2012); Wang, Chao; Liu, Lian-Long; Zhang, Ai-Ting; Xie, Peng; Lu, Jian-Jun; and Zou, Ziao-Ting; "Antimicrobial Effects of Zinc Oxide Nanoparticles on *Escherichia coli* K88", *African Journal of Biotechnology* 11(44), p 10248-10254, (2012)]. However, when these particles are "fixed" onto devices or surfaces such as coatings or composites, the level of antimicrobial performance is greatly diminished. There have been numerous attempts to incorporate ZnO into useful antimicrobial products, and even though antimicrobial effects are claimed, they are most often trivial. For instance, dental implants containing 10% ZnO nanoparticles showed only a 80% (<1 log) reduction of bacteria (Sevinc, Berdan, Aydin, and Hanley, Luke; "Antimicrobial Activity of Dental Composites Containing Zinc Oxide Nanoparticles", *Journal of Biomedical Materials Research, Part B, Applied Biomaterials* 94(1), p 22-31 (2011). One study reported "significant" reductions of bacteria by incorporating ZnO nanoparticles into PVC composites; however, the actual measured reduction was less than 50%, even when the composites contained 75% ZnO (Seil, Justin T.; and Webster, Thomas J.; "Zinc Oxide Nanoparticle and Polymer Antimicrobial Biomaterial Composites", MRS Proceedings 1316, (2010). Zinc oxide-filled UHMWPE composites showed only "slight inhibition" of *Staph. aureus* (Chang, B. P.; Akil, H. Md.; Nasir, R. Md.; and Nurdijati, S.; "Mechanical and Antimicrobial Properties of Treated and Untreated Zinc Oxide Filled UHMWPE Composites", *Journal of Thermoplastic Composite Materials* 24(5), p 653-667, (2011). ZnO nanoparticles coated onto textile fabrics gave only a 97% reduction of *Staph. aureus* (SA), and 87% reduction of *E. coli*, prior to any laundering (Singh, Gagandeep; Joyce, Eadaoin M.; Beddow, James; and Mason, Timothy J.; "Evaluation of Antimicrobial Activity of ZnO Nanoparticles Coated Sonochemically onto Textile Fabrics", *Biotechnology and Food Sciences* 2(1), p 106-120, (2012). A similar textile study found almost identical low reduction levels, and efficacy against EC dropped to just 40% after only one laundering (Rajendran, R.; Balakumar, C.; Ahammed, Hasabo A.; Mohammed, Jayakumar S.; Vaideki, K.; and Rajesh, E. M.; "Use of Zinc Oxide Nano Particles for Production of Antimicrobial Textiles", *International Journal of Engineering, Science and Technology* 2(1), p 202-208, (2010). Silicon wafers coated with ZnO showed only a 10% reduction in 24-hour biofilm formation (Gittard, Shaun D.; Perfect, John R.; Montiero-Riviere, Nancy A; Wei, Wei; Jin, Chunming; and Narayan, Robert, J.; "Assessing the Antimicrobial Activity of Zinc Oxide Thin Films Using Disk Diffusion and Biofilm Reactor", *Applied Surface Science* 255(11), p 5806-5811, (2009). The point here is that although ZnO, even in nanoparticulate form, is widely touted as having antimicrobial properties, it is relatively ineffective when incorporated into coatings or composites. The current invention will increase the antimicrobial efficacy of coatings containing ZnO by a few orders of magnitude (to at least the 3-log to 6-log level) via reacting the coatings with cleaning agents comprising HP.

The exact mechanism for the antimicrobial effect of ZnO is still somewhat of a mystery (Xie 2011, Zhang, Lingling; Jiang, Yunhong; Ding, Yulong; Daskalakis, Nikolaos; Jeuken, Lars; Povey, Malcolm; O'Neill, Alex J.; and York, David W.; "Mechanistic Investigation into Antimicrobial Behavior of Suspensions of ZnO Nanoparticles against *E. coli*", *Journal of Nanoparticle Research* 12(5), p 1625-1636, (2010); however, it is widely known that ZnO can generate hydrogen peroxide and other reactive oxygen species upon exposure to UV light (Xie 2011, Wang 2012). There is also evidence that ZnO can interact with, and cause disruption of, the bacterial cell walls.

Zinc oxide and hydrogen peroxide are known to react with each other to form "zinc peroxide". Zinc peroxide (ZP) is used as an oxidant, an antimicrobial, a blowing agent, and in the vulcanization of rubber, and its synthesis was patented in 1903 (U.S. Pat. No. 740,832). In 1951, Wood patented an improved method of producing zinc peroxide, which involved using sulfuric acid to essentially hydrolyze and "soften" the ZnO for improved yield (U.S. Pat. No. 2,563, 442). Later, Dana (U.S. Pat. No. 4,172,841) found that a solution of zinc acetate mixed with HP was useful for producing antimicrobial textiles. This chemistry essentially amounted to an in-situ deposition of ZP on the textile fabric. Similar results were found using both zirconium and magnesium salts (U.S. Pat. Nos. 4,174,418 and 5,656,037). Reaction of zinc oxide and/or zinc hydroxide with HP has been used to synthesize nanoparticles of ZP (Rosenthal-Toib, Liora; Zohar, Keren; Alagem, Meital; and Tsur, Yoed; "Synthesis of Stabilized Nanoparticles of Zinc Peroxide", *Chemical Engineering Journal* 136, p 425-429, (2008, Singh, Nahar; Mittal, Shelly; Sood, K. N.; Rashmi; and Gupta, Prabat K.; "Controlling the Flow of Nascent Oxygen Using Hydrogen Peroxide Results in Controlling the Synthesis of ZnO/ZnO2", *Chalcogenide Letters* 7(4), p 275-281, (2010). Zinc hydroxide (ZH) is easily formed in solution by reaction of zinc salts with sodium hydroxide, but is difficult or impossible to isolate in the dry state due to conversion to ZnO as it dries. ZnO on the other hand, can also be hydrolyzed back to ZH, and either ZnO or ZH can react with HP to form ZP, which can undergo a slow hydrolysis releasing HP in the presence of water. In other words, the ZH/ZnO/HP/ZP system essentially involves the sequestration of HP in a reversible manner. This slow release of HP is responsible for observed antimicrobial effect of ZP-based materials. Herein lies the key element of the current invention—it is a sequestration system for storage (sequestration) and controlled release of antimicrobially-effective amounts of hydrogen peroxide.

Several major companies have recently introduced HP-based cleaning products. Lysol (Reckitt Benckiser) has come out with an entire product line of household cleaning products based on hydrogen peroxide: "Guided by our LYSOL® Mission for Health, we are proud to introduce the innovative LYSOL® Power & Free™ product line to consumers who are in search of trusted, powerful cleaning agents that help to maintain a healthy home by using the very common, yet very effective household staple of hydrogen peroxide," (see http://www.prnewswire.com/news-releases/lysol-launches-line-of-hydrogen-peroxide-products-that-marks-a-new-era-in-household-cleaning-165569576.html). The label on Lysol's general purpose cleaner lists 0.9% HP as the active ingredient. Clorox has recently introduced a line of HP-based cleaners and wipes for hospital use—"Clorox Healthcare™ Hydrogen Peroxide Cleaner Disinfectants" (see http://www.cloroxprofessional.com/products/clorox-healthcare-hydrogen-peroxide-cleaner-disinfectants/at-a-glance/). The Clorox Material Safety Data Sheet lists "1 to 5%" as the concentration of HP.

SUMMARY

An embodiment of the present invention is a method of enhancing and regenerating durable antimicrobial activity of the surface of an article, wherein said method comprises the steps in sequence of:
  a. providing, on the surface of an article on which durable antimicrobial activity is desired, a polymer doped with a metal derivative,
  b. exposing the polymer doped with a metal derivative to a source of aqueous hydrogen peroxide for a time sufficient to permit an antimicrobially-enhancing amount of hydrogen peroxide to be sequestered thereon, and thereafter,
  c. removing the source of aqueous hydrogen peroxide, wherein said metal derivative comprises 1% to 50% (w/w) of the weight of the doped polymer, wherein said metal derivative is a hydroxide, an oxide, or a peroxide of a metal selected from the group consisting of zinc, magnesium, titanium, and zirconium,
  wherein the water absorbency of said polymer is between 0.5% and 20% (w/w), wherein said polymer doped with said metal derivative has been determined to be capable of sequestering hydrogen peroxide when exposed to said source of aqueous hydrogen peroxide;
  whereby said antimicrobial activity, when tested using ASTM Standard Method E2180 at least 24 hours after said removal of the source of hydrogen peroxide, provides at least a 3-log reduction of viable *Escherichia coli* bacteria greater than that of a corresponding surface of said polymer doped with said metal derivative which has not been exposed to hydrogen peroxide.

Optionally the above method may further comprise the step of;
  conducting an assay to confirm durable antimicrobial activity of the surface of said polymer doped with said metal derivative after said step c.

Preferably the metal derivative is selected from the group consisting of zinc hydroxide, zinc peroxide, zinc oxide, zinc oxide nanoparticles, and zinc oxide micron particles. More preferably the metal derivative is selected from the group consisting of zinc oxide nanoparticles and zinc oxide micron particles.

The metal derivative comprises 10% to 30% (w/w) of the weight of the doped polymer.

Suitable polymers of the invention are selected from the group consisting of polyacrylonitrile, acrylonitrile butadiene styrene (ABS) polymer, acrylic (PMMA), celluloid, cellulose acetate, ethylene-vinyl acetate (EVA), ethylene vinyl alcohol (EVOH), fluoropolymers (PTFE, FEP, PFA, CTFE, ECTFE, ETFE), ionomers, acrylic/PVC alloy, liquid crystal polymer (LCP), polyacetal (POM or Acetal), polyacrylates (acrylic), polyacrylonitrile (PAN or acrylonitrile), polyamide (PA or Nylon), polyamide-imide (PAI), polyaryletherketone (PAEK or Ketone), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetheretherketone (PEEK), polyetherketoneketone (PEKK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC); styrene-acrylonitrile (SAN), silicone polymers, thermoplastics, thermosets, elastomers; and copolymers, blends, and mixtures thereof.

A preferred polymer of the invention is selected from the group of polyurethanes, polyacrylates, and polyvinyl acetate.

Optionally, the doped polymer is a mixture that further comprises a hydrophilic acrylic polymer.

The source of aqueous hydrogen peroxide for the process desirably has a concentration of hydrogen peroxide between 0.5% and 10%. Preferably the concentration of hydrogen peroxide is between 1% and 5%. The hydrogen peroxide source may be a commercial cleaner containing at least 0.5% hydrogen peroxide.

Typically the doped polymer is exposed to hydrogen peroxide for 1 minute to 30 minutes. Longer exposure times are acceptable.

A preferred method to assay the level of sequestered hydrogen peroxide is a colorimetric spot test.

It is an embodiment of the invention to provide a regenerable antimicrobial coating comprising,
a. a metal derivative, wherein said metal derivative is a hydroxide, an oxide, or a peroxide of a metal selected from the group consisting of zinc, magnesium, titanium, and zirconium,
b. a polymer, wherein said polymer is doped with 1% to 50% (w/w) of said metal derivative,
c. sequestered hydrogen peroxide,
wherein the water absorbency of said polymer is between 0.5% and 20% (w/w), wherein said polymer doped with said metal derivative has been determined to be capable of sequestering hydrogen peroxide when exposed to said source of aqueous hydrogen peroxide; wherein the antimicrobial activity of said doped polymer can be regenerated on subsequent exposure to aqueous hydrogen peroxide,
whereby said antimicrobial coating, when tested using ASTM Standard Method E2180 at least 24 hours after preparation, provides at least a 3-log reduction of viable *Escherichia coli* bacteria greater than that of a corresponding coating which has not been exposed to hydrogen peroxide.

The regenerable antimicrobial coating comprises a polymer selected from the group consisting of polyacrylonitrile, acrylonitrile butadiene styrene (ABS) polymer, acrylic (PMMA), celluloid, cellulose acetate, ethylene-vinyl acetate (EVA), ethylene vinyl alcohol (EVOH), fluoropolymers (PTFE, FEP, PFA, CTFE, ECTFE, ETFE), ionomers, acrylic/PVC alloy, liquid crystal polymer (LCP), polyacetal (POM or Acetal), polyacrylates (acrylic), polyacrylonitrile (PAN or acrylonitrile), polyamide (PA or Nylon), polyamide-imide (PAI), polyaryletherketone (PAEK or Ketone), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetheretherketone (PEEK), polyetherketoneketone (PEKK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC); styrene-acrylonitrile (SAN), silicone polymers, thermoplastics, thermosets, elastomers; and copolymers, blends, and mixtures thereof.

Preferably the polymer is selected from the group of polyurethanes, polyacrylates, and polyvinyl acetate. The doped polymer may be a mixture that further comprises a hydrophilic acrylic polymer.

The regenerable antimicrobial coating may be a UV-curable coating, water-borne coating, or solvent-borne coating.

A typical regenerable antimicrobial coating comprising a UV-curable coating may further comprise a binder; curing agents; stabilizers; an acrylate oligomer; a urethane oligomer, a crosslinking agent such as tris (2-hydroxy ethyl) isocyanurate triacrylate and/or hexane diol diacrylate, a defoamer, a thermal stabilizer, a non-blocking slip additive, a photoinitiator, a near-UV photoinitiator, or mixtures thereof.

A typical regenerable antimicrobial coating comprising a water-borne coating may further comprise a self-crosslinking linking acrylic dispersion, a UV curable polyurethane dispersion, or a self-crosslinking polyurethane dispersion, and further comprise an alcohol, a glycol, defoamers, photoinitiators, thermal stabilizers, anti-oxidants, surfactants or mixtures thereof.

A typical regenerable antimicrobial coating comprising a solvent-borne coating may further comprise a solvent selected from the group of methylethylketone, ethanol, and mixtures thereof; and a coating polymer selected from the group consisting of polyvinyl acetate and polyvinyl acetate-crotonic acid copolymer; and further comprise defoamers, photoinitiators, thermal stabilizers, anti-oxidants, surfactants or mixtures thereof.

The article may be selected from the group consisting of medical implants; medical instruments or devices; hospital equipment; bed rails; table tops; bedpans; i.v. stands; lamp handles; blood pressure cuffs; dental equipment; surgical instruments; orthopedic devices; hot/cold packs; wheelchair cushions; doorknobs; bathroom fixtures; food preparation surfaces; equipment touch-screens; floor waxes; paints; inks; clear coats; varnish; kitchen equipment and tables in restaurants, schools, and other institutions; home appliances; and seats, armrests, railings, and tray tables for airlines and other public transportation.

DEFINITIONS

"Doping" as used herein refers the process of infusing, mixing, or otherwise adding a metal derivative to a polymer, which aids in changing the physical and chemical properties of the overall mixture.

"Antimicrobial" refers to the microbicidal or microbistatic properties of a compound, composition, formulation, article, or material that enables it to kill, destroy, inactivate, or neutralize a microorganism; or to prevent or reduce the growth, ability to survive, or propagation of a microorganism.

"Article" refers to a solid which may be rigid or flexible. In the context of the present invention, an article having a surface with durable antimicrobial activity is either capable of being coated with doped polymer or is comprised of such a doped polymer.

"Surface" refers to the common outside surface of the article including any coating thereon.

"Durable" means that the antimicrobial activity of an article remains after the article is treated. is washed or laundered one or more times, or that the antimicrobial activity persists for a significant portion of the expected useful lifetime of the treated substrate under normal use conditions.

"Metal Derivative" means an ion, salt, complex, hydrated ion, an ionic complex, a complex of an ion with hydrogen peroxide, a metal hydroxide species, a metal oxide species, or a metal peroxide species, or mixtures thereof, derived from one or more metallic elements for use in the invention. Preferred for use in this invention are metal derivatives of zinc, magnesium, or zirconium. For the purposes of this invention, the alkali metals (lithium, sodium, potassium, rubidium, cesium, and francium) are not included in the definition of "metal"; however, those elements also may be present in the formulations described herein.

DETAILED DESCRIPTION

This invention relates to regenerable antimicrobial coatings with durable antimicrobial efficacy for use in medical applications including implants, medical instruments or devices, and hospital equipment. The same coatings have broad utility in the consumer, industrial, and institutional markets for example for the preparation of floor waxes and paints having regenerable antimicrobial activity. The coating technology is based on sequestration of hydrogen peroxide (HP) by binders based on metal derivatives such as zinc oxide incorporated into the coatings. Coatings could be applied to key "frequent touch" areas where microbial contamination occurs—particularly those areas that can (or need to) be periodically cleaned. This includes, for example, countertops, bathroom fixtures, doorknobs, railings, and appliances. Materials to be coated would include, for example, metal, plastic, fiberglass, porcelain, and stone. These coated surfaces would be cleaned regularly with a cleaner containing HP. With each cleaning, the antimicrobial properties of the coated surfaces would be regenerated. The same polymers used for coatings can also be fabricated into polymer articles or device with durable antimicrobial activity, such as by casting, molding, extrusion, etc.

In accordance with the invention, zinc oxide particulates or fillers may be incorporated into coatings as binders for HP for use in applications where durable and regenerable antimicrobial protection is needed. Exposure of coated surfaces to HP solutions, or commercially-available HP-containing cleaning products can cause binding of HP to the zinc oxide particles; allowing HP to be sequestered within the coating after the surface has dried. This imparts a durable and long-lasting antimicrobial effect to the surface sufficient to reduce or eliminate the proliferation and spread of pathogenic organisms in-between cleaning cycles. Additionally, the antimicrobial effect is regenerated each time the surface is cleaned with an HP-containing solution.

An embodiment of the invention is a novel polymer coating which sequesters HP into a coated surface, keeping it there in active form even after the applied HP solution or cleaning product has long since dried or evaporated. This allows the surface to maintain long-lasting antimicrobial effects between cleanings. Data is presented herein to demonstrate that these coated and HP-exposed surfaces can kill greater than 99.9999% of microbes which contact the surface, even weeks after the HP exposure.

The polymer coatings bind hydrogen peroxide (HP), even after the surface has dried, thus maintaining sanitized surfaces and preventing microbial growth and the spread of disease. Although the coatings were developed with medical and hospital applications in mind, the potential for use in other areas are enormous, with broad utility in the consumer, industrial, and institutional markets. Examples of places where such coatings would have particularly helpful impact include bathroom fixtures in public restrooms; kitchen equipment and tables in restaurants, schools and other institutions; home appliances; or seats, armrests, railings, and tray tables for airlines and other public transportation. Such coatings could be easily implemented into existing manufacturing processes, retrofitted to existing equipment, or even sold as paints for DIY use. Widespread use of safe "green" HP technology would help to overcome the public's perception of antimicrobials as "toxic chemicals".

Another embodiment of this invention is a method to fabricate polymeric coatings or polymeric objects or articles which contain zinc oxide particles capable of binding and sequestering hydrogen peroxide in order to impart durable antimicrobial properties to the coatings, objects or articles even after the HP-based cleaning solution has dried or evaporated. The method comprises the steps of incorporating candidate particles into a model coating system, and then evaluating the antimicrobial efficacy of the coating after exposure to hydrogen peroxide. One may vary relevant parameters such as particle composition and size, particle loading, and polymer composition will be varied in order to optimize antimicrobial performance. Polymer composition may be varied by adjusting parameters such as hydrophilicity, crosslink density, or water-absorbing capacity.

The "self-sterilizing" surfaces resulting from the above outlined method would be broadly applicable in a wide range of places and applications, and widespread use would contribute significantly to the reduction of contaminated surfaces. The spread of disease and infection could be significantly reduced, leading to better health for all segments of the population, as well as a significant reduction in healthcare costs.

Potentially useful zinc oxide particles and nanoparticles are available from commercial suppliers. The zinc oxide particles vary not only in size, but also in shape, and crystallinity. Many are available in dry or suspended form. There are many different forms of ZnO that may be useful for the invention.

For example, the zinc oxide particles may be incorporated into either one or both of two model coating systems, a UV-curable 100%-solids acrylate coating system, or alternatively, a water-borne, UV-curable polyurethane (PU) dispersion system. These coatings may be in the form of inks, paint, varnish, clear-coats, or similar materials, and could be applied during manufacture of a device, or sold as post-treatments. Appropriate methods for evenly dispersing particulates into these coatings systems include processes such as simple mixing, media milling, high pressure homogenization, and the use of ultrasonics.

Test coatings may be fabricated on Mylar sheets or other substrates which are easily handled for testing. A coating on thin transparent Mylar (polyester) film is convenient for testing because it allows for easy cutting and testing of the coated material. Mixtures of zinc oxide particles and coating formulations found to have acceptable dispersion properties can readily be fabricated into coatings having approximately 5 to 20 microns in thickness.

Since ZnO is known to exhibit some level of antimicrobial activity on its own, it is helpful to evaluate baseline antimicrobial performance of coatings prior to HP exposure. The comparative antimicrobial performance of the as-produced coatings can be evaluated using two standard ASTM antimicrobial performance methods (Agar Slurry and Shake Flask methods) using both Gram+ and Gram− organisms (such as *Staph. aureus* and *E. coli*). The comparative testing of the coating after exposure to commercially-available HP-based cleaning products, or after prolonged exposure to higher concentrations of HP, provides a measure of the enhanced antimicrobial efficacy of the HP treated coatings.

Combinations of particles and coatings can be characterized by instrumental methods to determine the surface properties of the coatings. Coating characteristics (such as hydrophobicity and degree of crosslinking) can also be modified to enhance antimicrobial performance.

The general concept of this invention is to incorporate active metal oxide particulates such as zinc oxide into coatings for substrates such as medical devices such as implants, medical instruments or devices, and hospital equipment, or for manufacture of such articles from the polymers described herein. Examples of such substrates and devices include, for example: bed rails; table tops; bedpans; i.v. stands; lamp handles; blood pressure cuffs; dental equipment; surgical instruments; orthopedic devices, hot/cold packs, wheelchair cushions, Additionally, the invention is applicable for use on other common surfaces such as doorknobs, bathroom fixtures, food preparation surfaces, and equipment touch-screens—not just in hospitals, but also for institutional use (schools, prisons, restaurants, etc.), as well as in common household applications. Coatings can be applied at the time of manufacture of specific articles, devices, or surfaces. Alternatively, the required coatings can be applied at the point of use (much like paint, varnish, or floor wax).

The general concept of a regenerable ZnO binder for hydrogen peroxide locked into a polymer matrix can be widely applicable to almost any kind of existing coating system. Examples include 100% solids UV curable coatings, water-borne dispersions, solvent-borne coatings, extrusion coatings, and powder coatings. The invention is also applicable for use with all types of composites, or thermoplastics, and in virtually any molded, extruded, or melt blown type of application, such as thermoplastic polyurethanes, rubber, and silicone.

Regenerable antimicrobial coatings comprising 100% solids UV radiation curable coatings readily incorporate metal oxide particles using well known and studied milling processes. Additionally, the UV curable coatings allow greater flexibility in terms of targeting specific physical property attributes required for such a coating [Idacavage, Mike J; "Introduction to the Basics of UV/EB Chemistry and Formulations", SUNY ESF, Institute for Sustainable Materials and Manufacturing Webinar, Esstech, Inc. (2012)]. Some of those attributes are: control of surface characteristics such as hydrophobic/hydrophilic balance, scratch and abrasion resistance; speed of cure; weatherability; flexibility; ease of incorporation of inorganic oxides; high productivity; environmentally-friendly, low volatile organic compounds (VOC) emission; and adhesion to wide variety of substrates. UV curable coatings also have some shortcomings or areas of improvements to be taken into account, including: significant shrinkage upon cure leading to unacceptable adhesion to some non-porous low surface energy substrates; line of sight process which requires other strategies for dark cure of 3-dimensional parts; thick coatings, opaque coatings, and highly pigmented coatings are difficult to cure.

A variety of 100% solids UV-curable coating formulations are particularly useful as coating matrixes for the ZnO particulates. The coating formulations will typically comprise a blend of several acrylic monomers as well as curing agents, stabilizers, and other additives. Properties such as hardness, surface texture, hydrophobicity, and permeability can be modified by adjusting the ratios of key components. Typical components of the UV-curable coating include a binder such as an inert polyester resin; an acrylate oligomer such as polyethylene glycol diacrylate; a urethane oligomer such as an aliphatic urethane hexaacrylate oligomer; a crosslinking agent such as tris(2-hydroxy ethyl) isocyanurate triacrylate and/or hexane diol diacrylate. Typical additives include a defoamer, a thermal stabilizer, a non-blocking slip additive, a photoinitiator, and a near-UV photoinitiator. In the example below, an acrylic UV-curable coating formulation is designated as SS 1. For the purpose of our study the 100% solids UV curable coating solution was doped with the required amount of ZnO using a commercially available pre-dispersed Nano ZnO in a monomer such as TRPGDA.

Coatings from water-borne dispersions can be used advantageously for the design of a regenerable antimicrobial coating because of the variety of dispersions available, as well as ease of incorporation of metal oxide particles in the final coating. Water-borne dispersions have a superior environmental edge since there is very little VOC. Other advantages include: control of surface characteristics such as hydrophobic/hydrophilic balance; scratch and abrasion resistant coating upon crosslinking; ease of incorporation of inorganic oxides; high productivity; adhesion to wide variety of substrates; low or no shrinkage upon cure.

There are many types of commercially-available water-borne dispersions that can be used advantageously in a regenerable antimicrobial coating application. UV-curable acrylic dispersions or UV-curable polyurethane dispersions are particularly effective as matrixes for ZnO particulates. These types of systems show dry, non-tacky films before UV cure, and develop solvent-resistant and tough coatings after UV cure.

Another type of water-borne dispersion that can be used advantageously is a self-crosslinking acrylic or polyurethane dispersion (designated SXL). The SXL dispersions start the oxidative crosslinking process immediately upon removal of water. Using heat accelerates the process but room temperature crosslinking would proceed over a period of time and form tough, solvent-resistant coatings. The Nano ZnO dispersions can be incorporated quite easily in the SXL systems. Alternately, micro ZnO powders can also be dispersed in using various techniques described above.

A third type of polyurethane dispersion used are "physically drying" thermoplastic polyurethanes. The physically drying polyurethanes are fairly high MW polyurethane particles dispersed in water and form excellent films upon water removal. They attain their final property immediately upon drying. Similar to the UV curable and SXL systems above the ZnO dispersions can be easily incorporated in the physically drying PUD systems as well. The physically drying PUD can be further crosslinked if desired using a "2K" system adding an external crosslinking compound right before coating, although that might lead to shelf life issues.

A typical water-borne acrylic baseline coating formulation comprises water, a co-solvent such as isopropyl alcohol or a glycol ether, a binder, and a self-crosslinking linking acrylic dispersion. The acrylic dispersion is a polymerized system that has self-crosslinking or UV curable groups. Upon water removal the dispersion would coalesce and form non-tacky film. Over time the properties improve for the self-crosslinking. Upon UV curing, the properties improve for the UV curable acrylic. The formulation may further comprise additives such as defoamers, photoinitiators, thermal stabilizers, anti-oxidants, and surfactants. All of the components may be combined in different ratios to effect different surface properties.

A typical water-borne polyurethane baseline coating formulation comprises water, a co-solvent such as isopropyl alcohol or a glycol ether; a binder, a UV-curable polyurethane dispersion. The polyurethane dispersion is a high molecular weight polyurethane in a stable dispersion that has self-crosslinking or UV curable groups. Upon water removal the dispersion would coalesce and form non-tacky film. Over time the properties improve for the self-crosslinking. Upon UV curing, the properties improve for the UV curable polyurethane. The formulation may further comprise additives such as defoamers, photoinitiators, thermal stabilizers, anti-oxidants, and surfactants. All of the components may be combined in different ratios to effect different surface properties.

A third type of binder system shown as an example herein is solvent-borne coatings. Coatings based on a solid, thermoplastic, ultrahigh molecular homopolymer polyvinylacetate resins gave clear, flexible films with good gloss and resistant to oil and grease. Structure of ultrahigh molecular homopolymer polyvinylacetate resins (called Vinnapas UW4 FS) is as shown in Formula 1.

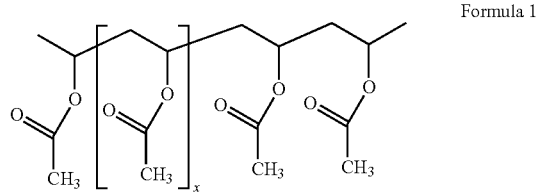

Formula 1

The resin was dissolved in MEK at 30% solids to give high viscosity liquid. It was further modified with a surface active wetting agent (Byk3440). This stock solution was XR-NSF-SB-F1 (SB-F1 for short). SB-F1 was then doped with a solvent-based Nano ZO in methoxypropylacetate.

However, for the purpose of the present invention we will exemplify water-borne UV-curable acrylics, UV-curable polyurethane dispersions (PUD). These types of systems show dry, non-tacky films before UV cure, and develop solvent-resistant and tough coatings after UV cure. Two baseline coating systems (designated as WBF1 and WBF2) were used as a matrix for the ZnO particulates. These contain the acrylic or PU resins as well as co-solvents, and other additives, which can be combined in different ratios to effect different surface properties.

Coatings for both types of systems (UV-curable and water-borne) can be applied to transparent Mylar film substrates for initial testing. Suitable coating thickness can range from 10 to 25 microns. These two classes of base coatings are merely representative of coatings, thermoplastics, and polymer composites in general. These two classes of coatings can be used for a variety of real-world coating applications. Furthermore, the invention should be transferable to many other commercially important coating and fabrication systems.

Zinc oxide is commercially produced by oxidation of zinc vapor in air. The zinc precursor may be zinc metal (direct process), or zinc ores (indirect process). Zinc oxides with special properties (such as nanoparticles) have been made by chemical methods using zinc hydroxide intermediates (see for instance Rosenthal-Toib 2008, wherein a zinc peroxide intermediate was used). Because of the higher surface area of nanoparticles compared to micron-sized ZnO, it is expected that nanoparticles will provide higher antimicrobial efficacy due to the increased area for reaction with HP. Many ZnO nanoparticle variations are available commercially. For example, the 2011-13 Alfa-Aesar catalog lists approximately 30 different ZnO particulate products. A selection of potentially useful ZnO particulates can be chosen based on structure, chemical properties, morphology, and form. Some of these products are conveniently available in forms that lend themselves to direct incorporation into either of the two types of selected coating bases.

Pre-dispersed metal oxide nano-dispersions are commercially available, including NanoArc® ZnO nanoparticles from Nanophase Technologies, available as concentrated (30 wt %) dispersions in low viscosity acrylate monomers such as TPGDA (tripropyleneglycol diacrylate) and HDODA (1,6-hexanediol diacrylate). These can be directly incorporated into the 100% solids UV-curable coating system. Pre-dispersed ZnO nano-dispersions in water are available in the market. These include NanoArc® Zinc Oxide nanoparticles from Nanophase Technologies, available as concentrated (50 wt %) dispersions water. These pre-despersed metal oxide nano-dispersions in water can be easily incorporated, pH permitting, in most water-borne dispersions described above. A variety of other pre-made aqueous and non-aqueous dispersions, such as those modified with silane coupling agents, or with various dispersing agents, are also commercially available. Predispersed solvent-based Nano ZO was available in methoxypropylacetate called Nanobyk 3841.

It is also an embodiment of the invention to incorporate ZH directly into the coatings. HP is more reactive with zinc hydroxide (ZH) than with ZnO. However, zinc hydroxide is difficult to isolate in dry form since it converts to ZnO as water is taken away. Yet, ZH aqueous suspensions effectively can be added to the water-borne coating system. The process is as follows. ZH is synthesized by neutralization of zinc chloride/nitrate with sodium hydroxide, and used after washing to remove the salt by-products. As described above (U.S. Pat. No. 2,563,442), zinc oxide can be partially hydrolyzed to produce a "softer" and more reactive surface. For instance, treatment of ZnO particles with sulfuric acid should produce a particle surface with higher reactivity towards HP. For this purpose a larger ZnO powder (micron size range) is used in order to facilitate handling and prevent complete dissolution of the particle. After washing with water, these surface-modified ZnO particles can be combined with the water-borne coating system.

Polymerizable metal acrylates such as zinc acrylate (available from Sartomer) can be used as part of the formulation to introduce metal ions into the coating system. These can then be further reacted with hydrogen peroxide as before. In fact, it is known that HP forms complexes with zinc acetate (similar in structure to zinc acrylate) to give antimicrobial properties after drying (U.S. Pat. No. 4,172,841). Metal acrylates; however, also create hydrophobic coatings, which may affect its efficacy.

Another embodiment of the invention is to utilize ZnO as the inorganic binder for HP. It is known that other metal oxides (such as Zr, Mg, and Ti) can also form complexes with HP. Particulates comprising oxides of these other metals can be identified, screened for sequestration of HP, and evaluated for antimicrobial efficacy.

As described above, potentially useful ZnO particles can be incorporated into coating systems such as UV 100% solids, or water-borne PU/Acrylic, or other solvent-borne coatings systems. Depending on the type of particle, a given particle may be useful in either one or both systems. For instance, premade dispersions in aqueous systems, laboratory-synthesized ZH, or acid-modified ZnO particles or polymerizable acrylate monomers are typically components in the water-borne system. Zinc acrylate monomers, or dispersions of ZnO in polymerizable acrylates are more suited for the non aqueous UV-curable 100% solids system. Similarly, the solvent-borne ZnO systems could be utilized for both the solvent-borne coatings as well as the 100% solids UV coatings. Uniform homogenous incorporation and thorough dispersion can be achieved with relatively simple mixing, as from an overhead mixer.

Many nano-based inorganic oxides can be incorporated into the water-borne dispersions solutions using high speed, high intensity mixing. In such instances a high shear homogenizer is desirable for this purpose. As much as 40-50% of the oxides can be uniformly incorporated using these techniques, and stay suspended for a definite period of time; however, re-mixing may be required after a certain shelf life period. Inorganic particulates can also be suitably dispersed using various dispersive aids. Milling or grinding of metal oxides, organic and inorganic pigments and other solids have been routinely accomplished using various types of milling processes. Those include amongst others media (or ball) milling, basket milling and 2-Roll or 3-Roll milling. Milling or grinding of metal oxides results in solutions which have significantly longer shelf life since the metal oxides are dispersed almost to the molecular state in the binder or solvents.

In most cases the size of the metal oxide nanoparticles allows UV- and visibly-transparent coatings, even for relatively high loadings. Thus, UV curing is as efficient with the added metal oxides having particle size lower than the wavelength of light. In fact, even for highly pigmented systems UV curing is efficient with the proper choice and range of photoinitiators. For initial screening, a particle loading of approximately 15-20 weight percent in the final coatings is preferred. Since the particles are relatively denser than the bulk coating, this represents a smaller volume fraction.

The coating/particle combinations can be prepared and evaluated for homogeneity, uniformity, and stability by making test coatings. Adjustments to formulations (such as adding more crosslinking agent or UV initiator, or adjusting coating conditions) can be made in order to ensure that fully-cured, uniform and reproducible coatings are produced.

Test coatings can be prepared on clear, thin, flexible Mylar sheets which are easily cut for testing. In general, coatings containing dispersed ZnO particulate can be applied using a Byk coating bar or a Meyer rod to produce coatings in the 10-20 micron size range. 100% solids coatings can be UV cured in a conveyer lamp oven, water-borne coatings can be air-dried prior to final UV crosslinking and the self crosslinking and physically drying systems can be cured by simply removing the water and/or solvent. Samples of each coating system without any ZnO incorporated can be used as negative controls in efficacy testing.

In order to provide a baseline for visualizing any enhancement of antimicrobial properties due to subsequent exposure to HP, it is necessary to first determine the baseline antimicrobial properties of the coatings. Two standard methods can be used, and initial testing can be against both a Gram− organism and a Gram+ organism. The 0% ZnO baseline coatings are used as negative controls for comparison of measured bacterial reduction. A desirable target for antimicrobial efficacy is a 3 to 6-log reduction in viable bacteria compared to an untreated control surface (i.e. a coating containing no ZnO, or a coating containing ZnO, but not exposed to HP), after the coating has been exposed to a HP solution or commercial cleaning product containing HP, tested at least 24 hours after the end of said exposure (i.e. a durable antimicrobial activity).

The coatings can be exposed to HP solutions prior to retesting for antimicrobial activity using the same two methods as described above. Although one embodiment of the invention is to show that coatings can be made active using the relatively low HP concentration in a commercial product (such as Lysol 0.9%HP active), it is also an embodiment to expose samples to higher concentrations of HP and compare results. A typical testing protocol is to expose samples of coatings to 10% and 3% HP solutions (optionally, with surfactant to enhance wetting of surface, and to mimic the effect of detergent in the commercial cleaning products). The samples are immersed in HP solutions for from 5 to 60 minutes then removed and allowed to air dry.

Coating/particulate combination(s) showing the potential for sequestering antimicrobial HP can be selected for further optimization. Characterization of the selected coating will provide information which may be valuable for learning how to modify the coatings in a positive manner. The coatings may be analyzed using optical microscopy, SEM, and FTIR will show the distribution and orientation of ZnO on the coating surface. Monitoring of dyne levels (hydrophobicity) of the oxide doped coatings can be used to gage the efficacy of HP incorporation. It is expected that a higher surface of exposed ZnO will allow for more reaction with HP and thus higher efficacy. Back-scatter and EDX analysis can also show more precisely the availability of ZnO on the surface (as opposed to just the topography seen with SEM). Light abrasion of the surface may cause ZnO particles that are "buried" under the coating polymer to become surface active and enhance efficacy. This effect can be investigated by checking for enhanced antimicrobial activity after repeated rubbing with a slightly abrasive applicator (such as Scotch-Brite pad) containing HP cleaning solution.

Other ways the coatings or polymer articles or objects can be enhanced include adding a higher level of particulates, or by altering coating hardness, crosslinking, or hydrophobicity. Since the hydrogen peroxide needs to react with the metal oxide in the cured coating the hydrophilic/hydrophobic balance may be critical. This can be suitably targeted by the choice of monomers or oligomers which are polar, hydrophilic and even water soluble. Several oligomers based on polyethylene glycol are used in UV curable systems to create an anti-fog coating. These function very well as a hydrophilic surface to allow efficient absorption of hydrogen peroxide into the body of the coating and to react with the high surface area nano-metal oxides. The dyne level of the coating can thus be adjusted to target the hydrophilic/hydrophobic balance.

Besides the hydrophilic/hydrophobic balance, the coating roughness can also play a key role. Many additives are available such as flattening agents which impart matte character to the UV cured coating. Other additives such as micronized polypropylene waxes provide a unique texturizing effect to the coating increasing the likelihood of efficacy of reaction between hydrogen peroxide and the metal oxide dopant.

The amount of HP sequestered onto the surface of coatings is measured directly by using known titration techniques. These methods involve titration of fluids in contact with the coated surface using thiosulfate or permanganate, or by a colorimetric "spot-test" using similar reagents. For example, a droplet of reagent containing permanganate or iron ions is applied to a surface of the current invention after it has been exposed to HP. A color change will occur based on the presence or sequestered HP Additional antimicrobial characterization can be performed utilizing test methods described herein, and can include a wide range of pathogenic bacteria, including resistant strains such as MRSA and VRE. Other organisms that could be tested include *Enterococcus faecium, Escherichia coli, Pseudomonas aeruginosa,* and *Klebsiella pneumonia.* A time-kill study using *E. coli* and *S. aureus* can also be performed to determine the rate of induction of the antimicrobial effect. In addition, testing against selected fungal organisms (such as *Candida albicans* and *Aspergillus niger*) can be carried out using appropriate methods (such as ASTM G21).

In addition, the anti-viral efficacy of coated surfaces exposed to HP-based cleaning solutions can be measured against selected types of viruses using appropriate methods.

Preliminary life-cycle (extended use) testing of coatings can be done by evaluating basic antimicrobial efficacy of coatings subjected to repeated cleaning cycles (i.e. 25× and 50× with a scrubbing pad). Observations on the physical appearance and integrity of the coatings can be made.

Many different polymers may be used in the practice of this invention; however, it is necessary for the dispersed metal derivative to come into contact with the peroxide in order for a complex of the metal derivative and peroxide to form, thus sequestering the peroxide in the polymer so that it may be released later to provide antimicrobial effect. One skilled in the art will realize that the contact between metal derivative and peroxide will be maximized by using a higher concentration of peroxide and/or a longer contact time. The contact between metal derivative and peroxide will also increase as the amount of metal derivative dispersed in the polymer increases, and particularly as the amount of the metal derivative particles exposed or near the surface of the polymer increases. In order for particles of metal derivative covered by polymer (I.e. those particles below the surface) to come in contact with the peroxide, the peroxide must be able to penetrate (diffuse) into the polymer matrix. One factor that controls the penetration of peroxide into the polymer matrix includes hydrophilic character, since HP is a polar molecule like water. Another factor that controls the penetration of peroxide into the polymer matrix is crosslink density. Polymers with a lower crosslink density will allow better penetration of HP solution. These same factors will also allow release of sequestered HP later when it is needed for antimicrobial effect by allowing water back into the polymer matrix in a reversible manner so that peroxide can be unsequestered and diffuse to the polymer surface in a controlled manner.

However, extremely high hydrophilic character or low crosslinking (either alone or in combination) is undesirable, as it could lead to a high absorption of water, and extensive swelling (or even dissolution of) the polymer and loss of desirable polymer properties such as hardness or structural integrity. Thus, a balance of properties is required. Hydrophilic character can be increased by adding hydrophilic agents or wetting agents, which may be either polymeric agents or low molecular weight agents. For example, the water-borne formulations described in the examples herein demonstrate the enhanced efficacy manifested by adding hydrophilic polymers to a formulation. This can be seen by comparing samples WB F1 and WBF2 to WBF3 and WBF4 at a constant (20%) ZnO content—the antimicrobial activity of WBF3 and WBF4 is much higher due to increased hydrophilic character from adding a hydrophilic modifier (see for example data in Table 7 vs. Table 19). The amount of hydrophilic agent needed will vary based on the exact chemical structure of a particular polymer system. The overall effect of the incorporation of hydrophilic agent, or degree of crosslinking, on absorption of water (or peroxide solution) will be the percentage of water absorbed by the polymer. Since these factors affect different polymers to different extents, it is convenient to use the actual measured absorbance of the polymer to characterize these effects.

In general, a polymer which absorbs between 0.5% and 20% (w/w) water will be useful in the practice of this invention, as this allows for penetration of HP, but does not cause extensive swelling or degradation of the polymer. A preferred range is between 2% and 10% (w/w) absorption of water. A method such as ASTM D570 may be used to determine water absorbance of the base polymer, or the polymer with metal derivative dispersed therein.

Many different polymers are useful in the practice of this invention. The following is a partial list of polymers that can be used: Polyacrylonitrile, acrylonitrile butadiene styrene (ABS) polymer, Acrylic (PMMA), Celluloid, Cellulose acetate, Ethylene-Vinyl Acetate (EVA), Ethylene vinyl alcohol (EVOH), Fluoropolymers (PTFE, FEP, PFA, CTFE, ECTFE, ETFE), Ionomers, acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone), Polybutadiene (PBD), Polybutylene (PB), Polybutylene terephthalate (PBT), Polycaprolactone (PCL), Polychlorotrifluoroethylene (PCTFE), Polyethylene terephthalate (PET), Polycyclohexylene dimethylene terephthalate (PCT), Polycarbonate (PC), Polyhydroxyalkanoates (PHAs), Polyketone (PK), Polyester, Polyethylene (PE), Polycarbonate (PC), Polyetheretherketone (PEEK), Polyetherketoneketone (PEKK), Polyetherimide (PEI), Polyethersulfone (PES), Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polypropylene (PP), Polystyrene (PS), Polysulfone (PSU), Polytrimethylene terephthalate (PTT), Polyurethane (PU), Polyvinyl acetate (PVA), Polyvinyl chloride (PVC), Polyvinylidene chloride (PVDC); Styrene-acrylonitrile (SAN), Silicone polymers, Thermoplastics, Thermosets, and Elastomers; as well as copolymers, blends, and mixtures of the above-listed polymers.

In light of the general disclosure provided herein above, with respect to the manner of practicing this inventive method, those skilled in the art will appreciate that this disclosure enables the practice of the inventive method as defined in the attached claims. However, the following experimental details are provided to ensure a complete written description of this invention, including the best mode thereof. However, it will be appreciated that the scope of this invention should not be construed in terms of the specific examples provided. Rather, the scope of this invention is to be apprehended with reference to the claims appended hereto, in light of the complete description of this inventive method constituted by this entire disclosure.

EXAMPLES

The following examples are representative of the invention and exemplify experiments using a commercially-available ZnO powder.

Example 1

Preparation of Antimicrobial ZnO Powder

Commercially available ZnO powder was mixed with water to make a 1% aqueous dispersion and was treated with 3% hydrogen peroxide solution. The mixture was stirred for 15 minutes and then dried to obtain the treated ZnO powder. The treated dried ZnO powder was found to have an antimicrobial effect which was approximately 2-logs greater than dried ZnO powder which had not been exposed to HP.

Example 2

Preparation of 100% Solids UV Stock Solution

The 100% solids UV stock solution, acrylic UV-curable coating formulation designated as SS1, was mixed for 15 minutes until it is homogenous. The stock solution in the proper portion is then mixed with a dispersive aid and small particle size (in the nano range) Zinc Oxide using a high speed mixer to obtain a slurry comprising about 20% ZnO. The slurry is then incorporated into either a 2-roll mill or media milling machine to grind the oxide particles until no particles are seen in the Hegman grind gage. Alternately, the milled solution may be dissolved in a solvent and particle size analysis carried out. The above milled 100% solids solutions are rod coated onto polyester substrates. The coated substrate are sent into an in-line UV curable unit at 20 ft./min using a 300 WPI power setting. If the surface is slightly tacky the UV curing can be repeated (20 fpm/300 wpi) to obtain a completely dry and non-tacky surface. A similar control can also be coated and cured using just the SS1 stock solution without ZnO. Comparative antimicrobial studies can be then carried out on the control sample (w/o ZnO), an untreated sample (with ZnO), and a sample (with ZnO) treated with hydrogen peroxide solution.

Example 3

Preparation of Water-Borne UV Curable Polyurethane Dispersion (PUD)

The UV curable PUD stock solution designated as WBS1 is mixed for 15 minutes until it is homogenous. The above WBS 1 stock solution in the proper portion is then mixed with a pre-milled ZnO solution in water using a high speed mixer to obtain a final solution having about 10% nano ZnO based on dry weight of the coating. The above UV PUD solution doped with nano ZnO is rod coated onto polyester substrates. The coated substrate is dried at 110° C. for 2-5 minutes until it is completely dry to touch. The dried coated substrate is then sent into an in-line UV curable unit at 20 ft./min using a 300 WPI power setting to completely cure the coating. A similar PUD control can be coated, dried, and cured using just the WBS1 stock solution without the nano ZnO. Comparative antimicrobial studies can be then carried out on the control sample (w/o nano ZnO), an untreated sample (with nano ZnO), and a sample (with nano ZnO) treated with Hydrogen Peroxide solution.

Example 4

Preparation of Zinc Hydroxide in Ethanol

The reaction product of a mixture of zinc chloride and zinc nitrate with sodium hydroxide was dispersed in additional water and allowed to undergo several cycles of settling and decanting. This process removes the salt (NaCl and $NaNO_3$) by-products present in the binder. A portion of this washed ZH aqueous suspension was saved for use in experiments. Using another portion, the water was then replaced with ethanol for several cycles in order to achieve zinc hydroxide in dry ethanol. The ethanol of the resulting zinc hydroxide mixture can be displaced using HDODA (1,6-hexanediol diacrylate) monomer. This could not be done directly because water and HDODA are not miscible. The ethanol serves as an intermediate.

Example 5

Preparation and Use of Nano-ZnO in 100%-Solids UV-Cured Coating Compositions Two different stock solutions were prepared XR-NSF-UV-F 1 and XR-NSF-UV-F2. Both stock solutions are designed to be hydrophilic due to the addition of a hydrophilic (water soluble) oligomer at 30-40%.

| XR-NSF-UV-F1 Formulation | | |
| --- | --- | --- |
| Component | Function | Weight % |
| Genomer 6083/HD | Inert resin (polyurethane) in monomer. Main binder for the coating. | 50.0 |
| MIRAMER M280 | Hydrophilic Oligomer | 41.3 |
| Tego Foamex N | Defoamer | 1.0 |
| G16 stabilizer | Oxidative Stabilizer | 0.5 |
| MP1200 Wax | Detack | 1.1 |
| Esacure ONE | Photoinitiator | 3.6 |
| TPO | Photoinitiator | 1.2 |
| Byk Silclean 3710 | Surface Active Agent | 1.2 |
| Total | | 100.0 |

| XR-NSF-UV-F2 Formulation | | |
| --- | --- | --- |
| Component | Function | Weight % |
| Genomer 6083/HD | Inert resin (polyurethane) in monomer. Main binder for the coating. | 30.0 |
| Genomer 4690 | Aliphatic urethane hexaacrylate Higher Crosslinking | 30.0 |
| MIRAMER M280 | Hydrophilic Oligomer | 31.2 |
| Tego Foamex N | Defoamer | 1.0 |
| G16 stabilizer | Oxidative Stabilizer | 0.5 |
| MP1200 Wax | Detack | 1.0 |
| CPK | Photoinitiator | 5.0 |
| Byk Silclean 3710 | Surface Active Agent | 1.2 |
| Total | | 100.00 |

The respective Zinc Peroxide (ZP), Zinc Hydroxide (ZH), and Zinc Oxide (ZO) solutions (in 1,6-hexanediol diacrylate (HDODA) or tripropylene glycol diacrylate (TRPGDA)) were then added into the stock solutions targeting either 10%, 15% or 20% pigment loadings as shown in the Table 1 below (PHR added is amount of pigment solutions based on 100 grams of stock solution to get the % loadings desired). The ZH could only be added at 10% due to the lower concentration (18.5%).

TABLE 1

| 100% Solids UV Curable Coating Compositions | | | | | | |
| --- | --- | --- | --- | --- | --- | --- |
| Coating | Stock Solution | Zn Solution | Pigment Loading | % Pigment | PHR added | For 20 g stock |
| UV-F1 | UV-F1 | | | | | |
| UV-F2 | UV-F2 | | | | | |
| F1-15ZP | UV-F1 | 30% ZP HDODA | 15 | 30 | 100 | 20.0 |
| F2-15ZP | UV-F2 | 30% ZP HDODA | 15 | 30 | 100 | 20.0 |
| F1-10ZH | UV-F1 | 18.5% ZH HDODA | 10 | 18.5 | 117.6 | 23.5 |
| F2-10ZH | UV-F2 | 18.5% ZH HDODA | 10 | 18.5 | 117.6 | 23.5 |
| F1-20ZO | UV-F1 | 30% ZO TRPDA | 20 | 30 | 200 | 40.0 |

TABLE 1-continued

100% Solids UV Curable Coating Compositions

| Coating | Stock Solution | Zn Solution | Pigment Loading | % Pigment | PHR added | For 20 g stock |
|---|---|---|---|---|---|---|
| F2-20ZO | UV-F2 | 30% ZO TRPDA | 20 | 30 | 200 | 40.0 |
| F1-15ZO | UV-F1 | 30% ZO TRPDA | 15 | 30 | 100 | 20.0 |
| F2-15ZO | UV-F2 | 30% ZO TRPDA | 15 | 30 | 100 | 20.0 |

*ZO is NanoArc® ZN-2660

For most of the above coatings two different rod sizes Rod#8 (8R) and Rod#16 (16R) were used in order to see the effect of coating thickness on sequestration ability. The theoretical coating weight (CW) would be around 18.3 g/m$^2$ for 8R and around 36.6 g/m$^2$ for 16R. This is very approximate and would probably be 25-50% lower due to low viscosities of all solutions. Assuming the density of the coating to be 1.0 g/cc, the coating thickness would be 1 micron for CW of 1 g/m$^2$. However, since the density of the coating is >>1.0 g/cc due to the pigment loading, the conversion would be further affected to the low end of the coating thickness. Thus, we estimate the coating thickness to be around 10-15 microns for the 8R and 25-30 microns for 16R.

Observations from the UV Curable Coatings:
All coatings were done on a polyester substrate from SKC Films called SH41
As expected the F2 formulation had higher crosslink density than F1 as seen from the "shrinkage" upon cure leading to the polyester film curling up
All coatings were structured. This might be a function either of the particle size or inadequate milling of the additive with the UV solution. Milling results in molecular interaction between the nanoparticle and the UV resin
Not surprisingly, the ZP and ZH were particularly structured since they had higher particle size. The ZO with particle size around 20-40 NM was found to be less structured
Even the structured coatings show good scratch resistance and adhesion to the PET substrate
The structure may not necessarily be bad since it will have higher ability to absorb HP on the surface due to "micro-roughness"
The dosage used for UV curing of most coatings was around 0.9 J/Cm$^2$ (see exception below) by using 2 passes at 30 fpm at 300 WPI power
The Zinc Oxide coating was very difficult to cure, especially the 20% loading at 0.9 J/Cm$^2$. We had to use 5× the dosage (~5 J/Cm$^2$) to get decent cure. This was not surprising since ZnO are known UV attenuators and in fact are used as weathering additives to prevent damage from sunlight (see below)

Example 6

Antimicrobial Activity of Samples of Example 5

The samples of Example 5 were exposed to 10% aqueous HP for one hour, then shaken to remove excess droplets of solution and allowed to dry for at least 72 hours at room temperature. The samples were tested for antimicrobial efficacy against Staph. aureus using ASTM E2180 "agar slurry" method, with an overnight exposure time. This same method is used in all of the following examples. All samples showed a "full kill" of SA (5.49 log reduction), as indicated in Table 2 below, in comparison to an untreated Mylar film not exposed to HP. Note that the term "Overnight" in the antimicrobial results refers to the difference in bacterial population between the sample and a negative control sample inoculated with the same bacterial load after both have been incubated overnight. The term "t=0" refers to the difference between the bacterial population on the sample after overnight incubation vs. the initial amount of inoculation, as measured on a negative control sample at t=0. Unless otherwise noted, all average log reductions are the average of three sample replicates.

TABLE 2

Antimicrobial Efficacy Against Staph. aureus

| Sample versus SA | HP Exposure | Avg Log Reduction Overnight | Avg Log Reduction t = 0 |
|---|---|---|---|
| 081213; Sample 5, F1-10ZH (F1 stock loaded with 10% ZH) | Exposure to 10% HP | 5.49* ± 0.00 | 5.24* ± 0.00 |
| 081213; Sample 6, F2-10ZH | Exposure to 10% HP | 5.49* ± 0.00 | 5.24* ± 0.00 |
| 081213; Sample 7, F1-20ZO (F1 stock loaded with 20% nano-ZO) | Exposure to 10% HP | 5.49* ± 0.00 | 5.24* ± 0.00 |
| 081213; Sample 8, F2-20ZO | Exposure to 10% HP | 5.49* ± 0.00 | 5.24* ± 0.00 |
| 081213; Sample 9, F1-15ZO | Exposure to 10% HP | 5.49* ± 0.00 | 5.24* ± 0.00 |
| 081213; Sample 10, F2-15ZO | Exposure to 10% HP | 5.49* ± 0.00 | 5.24* ± 0.00 |
| Sample 1, -UV-F1 Control | Exposure to 10% HP | 5.49* ± 0.00 | 5.24* ± 0.00 |
| Sample 2, UV-F2 Control | Exposure to 10% HP | 5.49* ± 0.00 | 5.24* ± 0.00 |
| Uncoated Mylar sheet, Sample 11 | Exposure to 10% HP | 5.49* ± 0.00 | 5.24* ± 0.00 |
| Untreated Mylar sheet, Sample 11 | No HP exposure | No kill | No kill |

The samples of Example 5 were then tested against E. coli (EC). Control samples and uncoated Mylar showed essentially no kill, as expected. Samples containing ZH and ZO showed full-kill (6.67 log-reduction) of EC. Results are shown in Table 3 below.

TABLE 3

Antimicrobial Efficacy Against E. coli

| Sample versus EC | HP Exposure | Avg Log Reduction Overnight | Avg Log Reduction t = 0 |
|---|---|---|---|
| 081213; Sample 5, F1-10ZH (F1 stock loaded with 10% ZH) | Exposure to 10% HP | 6.67* ± 0.00 | 5.18* ± 0.00 |
| 081213; Sample 6, F2-10ZH | Exposure to 10% HP | 6.67* ± 0.00 | 5.18* ± 0.00 |
| 081213; Sample 7, F1-20ZO (F1 stock loaded with 20% nano-ZO) | Exposure to 10% HP | 6.67* ± 0.00 | 5.18* ± 0.00 |
| 081213; Sample 8, F2-20ZO | Exposure to 10% HP | 6.67* ± 0.00 | 5.18* ± 0.00 |

TABLE 3-continued

Antimicrobial Efficacy Against E. coli

| Sample versus EC | HP Exposure | Avg Log Reduction Overnight | Avg Log Reduction t = 0 |
|---|---|---|---|
| 081213; Sample 9, F1-15ZO | Exposure to 10% HP | 6.67* ± 0.00 | 5.18* ± 0.00 |
| 081213; Sample 10, F2-15ZO | Exposure to 10% HP | 6.67* ± 0.00 | 5.18* ± 0.00 |
| Sample 1, Control (0% ZnO) | Exposure to 10% HP | 0.33 | −1.17 |
| Sample 2, UV-F2 Control (0% ZnO) | Exposure to 10% HP | 0.26 | −1.24 |

Example 7

Preparation of Water-Borne Coatings and Solvent-Borne Coatings Containing nano-ZnO Two different approaches were used for water-borne coatings.

(a) Water-Borne UV Curable Polyurethane Dispersion (UV PUD): Water-borne UV PUD from Allnex called Ucecoat 7689 was suitably modified with water-based photoinitiators, anti-oxidants and surface active agents (surfactants). A co-solvent (IPA) was also used in small quantities to help coatability. This stock solution was XR-NSF-WB-F1 (WB-F1 for short).

XR-NSF-WB-F1 UV Curable PUD Formulation

| Component | Function | Weight % |
|---|---|---|
| IPA | Co-solvent | 3.00 |
| UCECOAT 7689 | Water-borne UV Curable PUD 35% in water | 89.70 |
| M380 | Hydrophilic Oligomer | 5.00 |
| GENOCURE* LBC | Oxidative Stabilizer | 1.73 |
| Irganox ® 1520 | Photoinitiator | 0.32 |
| Dynol 607 | Surface Active Agent | 0.21 |
| Total | | 100.0 |

WB-F1 was then doped with Nanobyk 3840 to get 10% and 20% ZO loadings respectively as shown in Table 4. The coatings were coated on polyester substrates as summarized below.

(b) Water-Borne Self-Crosslinking Polyurethane Dispersion (SXL PUD): Water-borne SXL PUD from Alberdingk called U 915 is a self-crosslinking polycarbonate/polyester polyurethane dispersion. U915 was modified with only a surfactant since it already has a coalescing solvent. This stock solution was XR-NSF-WB-F2 (WB-F2 for short).

XR-NSF-WB-F2 Self-Crosslinking Formulation

| Component | Function | Weight % |
|---|---|---|
| IPA | Co-solvent | 3.00 |
| Alberdingk U915 | Water-borne SXL PUD 34% in water | 96.80 |
| Dynol 607 | Surface Active Agent | 0.21 |
| Total | | 100.0 |

WB-F2 was then doped with the water-borne Nano ZO (Nanobyk 3840) to get 10% and 20% ZO loadings respectively as shown in Table 4. The coatings were coated on polyester substrates as summarized below.

TABLE 4

Water-Borne Coating Compositions

| Coating | Stock Solution | Nano Zn Solution | Amount/binder solids | % NV | PHR added | For 20 g | % Solids | CW, 8R Wet 18.3 gsm |
|---|---|---|---|---|---|---|---|---|
| WB-F1 | WB-F1 | | | | | | | |
| WB-F2 | WB-F2 | | | | | | | |
| WBF1-20ZO | WB-F1 | 40% water | 10 | 40 | 9.7 | 1.9 | 38.77 | 7.10 |
| WBF2-20ZO | WB-F2 | 40% water | 20 | 40 | 19.3 | 3.9 | 38.87 | 7.11 |
| WBF1-10ZO | WB-F1 | 40% water | 10 | 40 | 8.3 | 1.7 | 33.65 | 6.16 |
| WBF2-10ZO | WB-F2 | 40% water | 20 | 40 | 16.6 | 3.3 | 34.10 | 6.24 |

Two different formulatory approaches were used for solvent-borne coatings.

(c) Solvent-borne Coatings Based on Thermoplastic Polyvinylacetate (VINNAPAS® UW 4 FS): High MW Polyvinyl acetate (VINNAPAS from Wacker) has been used as coatings and adhesives. Coatings based on Polyvinylacetate resins give clear, flexible films with good gloss and are resistant to oil and grease. VINNAPAS® UW 4 FS is a solid, thermoplastic, ultrahigh molecular homopolymer.

The resin was dissolved in MEK at 30% solids to give high viscosity liquid. It was further modified with a surface active wetting agent (Byk3440). This stock solution was XR-NSF-SB-F1 (SB-F1 for short). SB-F1 was then doped with the solvent-based ZO Nanobyk 3841 to get 10% and 20% ZO loadings respectively as shown in Table 5.

(d) Solvent-borne Coatings Based on Polyvinylacetate-Crotonic Acid Copolymer (VINNAPAS® C 305): Polyvinylacetate-Crotonic Acid Copolymer (VINNAPAS C305 from Wacker) has been used as coatings and adhesives. VINNAPAS® C 305 is a physically drying, thermoplastic binder. The —COOH groups in C305 could potentially give hydrophilic coatings.

The resin was dissolved in MEK at 40% solids to give high viscosity liquid. It was further modified with a surface active wetting agent (Byk3440). This stock solution was XR-NSF-SB-F2 (SB-F2 for short). SB-F2 was then doped with the solvent-based ZO Nanobyk 3841 to get 10% and 20% ZO loadings respectively as shown in Table 5. All the doped solutions based on C305 gelled. Most likely the ZnO formed a complex with the Crotonic acid and created crosslinked networks. Thus, no coatings were made with SB-F2 solutions.

TABLE 5

Solvent-Borne Coating Compositions

| Coating | Stock Solution | Nano Zn Solution | Amount/ binder solids | % Nano- particle | % Resin Solution | PHR added | For 20 g | % Solids | CW, 8R Wet 18.3 gsm |
|---|---|---|---|---|---|---|---|---|---|
| SB-F1 | | | | | | | | | |
| SBF1-10ZO | SB-F1 | 40%* | 10 | 40 | 30 | 7.5 | 1.5 | 30.70 | 5.62 |
| SBF1-20ZO | SB-F1 | 40%* | 20 | 40 | 30 | 15 | 3 | 31.30 | 5.73 |
| SBF2-10ZO | SB-F2 | 40%* | 10 | 40 | 40 | 10 | 2 | 40.00 | 7.32 |
| SBF2-20ZO | SB-F2 | 40%* | 20 | 40 | 40 | 20 | 4 | 40.00 | 7.32 |

*All NanoZinc solutions were 40% NB3841 in methoxypropylacetate.

For most of the above coatings we used only one rod size Rod#8 (8R), although 20R was also looked at for couple of coatings. The theoretical wet CW would be around 18.3 g/m² for 8R. The theoretical dry CWs are then calculated based on % solids and given in the respective Tables above. General observations for the water-borne and solvent-borne coatings of Example 7 were as described below.
- All coatings were made on a PET substrate from SKC Films called SH41.
- Compared to the UV-cured coatings of Example 5 the water-borne and solvent-borne systems were significantly more uniform in appearance and texture.
- The UV PUD formulations (WB-F 1) are "physically dry" after drying the water off. However, the final physical property was only assumed after UV curing. The SXL PUD formulations (WB-F2) were also "physically dry" after drying the water off and assumed most of its physical property after drying due to self-crosslinking. However, the final physical property is only assumed after some unknown period due to continued self-crosslinking.
- The solvent borne systems are physically drying after solvent removal (2 mins at 180 C) and assumes its final physical property immediately due to its high MW nature.
- The coatings made with nano-ZnO were substantially transparent, or clear to slightly hazy.

Example 8

Antimicrobial Activity of Samples of Example 7

The water-borne coating systems (samples designated with prefix "W") and solvent-borne coatings systems (samples designated with prefix S) of Example 7 were tested for antimicrobial activity using ASTM E2180 "agar slurry" method. In particular samples WB-F2, WBF1-20ZO, WBF1-10ZO, SBF1-20ZO, and SBF1-10ZO from Example 7 as well as samples UV-F2, F2-10ZH, F2-15ZO, and a blank Mylar film 7 were used for the present study. The selected samples were exposed to 3% HP for one hour, and then tested for antimicrobial efficacy against EC after drying for at least 24 hours. Samples UV-F2, F2-10ZH, F2-15ZO, WBF1-20ZO, and a blank Mylar film were also tested without exposure to HP. The results are shown in Table 6. All samples NOT exposed to HP showed essentially zero antimicrobial efficacy.

The data confirm that ZnO, even nano-ZnO has very little inherent value as a solid antimicrobial surface, despite the efficacy seen when these particles are dispersed or suspended in liquid form. Interestingly, the uncoated Mylar film continues to show minor antimicrobial efficacy (~2-log reduction) after exposure to 3% HP for one hour; however, subsequent experiments revealed that this is not always reproducible. Note that the samples were not rinsed prior to drying. None of the water-borne (WB) samples showed any antimicrobial efficacy after exposure to 3% HP. For the solvent based (SB) samples, moderate efficacy (~4-log) was found for the higher (20% ZnO) loading, but no efficacy was observed at the lower (10% ZnO) loading. This sample may show efficacy if higher HP concentrations or longer exposure times were used. For the 100%-solids UV system, no efficacy was found for 10% ZH, but great efficacy (full kill of 6.6 logs) was found with 15% ZnO.

TABLE 6

Antimicrobial Activity of Water-Borne Compositions Against EC

| Sample versus EC | HP Exposure | Log Reduction Overnight | Log reduction t = 0 |
|---|---|---|---|
| 082613; Sample 2, UV-F2 Control | After exposure to 3% HP | 0.37 ± 0.15 | −1.11 ± 0.15 |
| 082613; Sample 2u, UV-F2 Control | No HP exposure | 0.08 ± 0.06 | −1.41 ± 0.06 |
| 082613; Sample 6, F2-10ZH | After exposure to 3% HP | 0.06 ± 0.41 | −1.43 ± 0.41 |
| 082613; Sample 6u, F2-10ZH | No HP exposure | −0.18 ± 0.36 | −1.67 ± 0.36 |
| 082613; Sample 10, F2-15ZO | After exposure to 3% HP | 6.63* ± 0.00 | 5.14* ± 0.00 |
| 082613; Sample 10u, F2-15ZO | No HP exposure | −0.19 ± 0.15 | −1.67 ± 0.15 |
| 082613; Sample 11, Blank Mylar Control | After exposure to 3% HP | 2.02 ± 0.66 | 0.53 ± 0.66 |
| 082613; Sample 11u, Blank Mylar Control | No HP exposure | −0.20 ± 0.17 | −1.69 ± 0.17 |
| 082613; Sample W3, WBF1-20ZO | After exposure to 3% HP | 0.07 ± 0.01 | −1.42 ± 0.01 |
| 082613; Sample W3u, WBF1-20ZO | No HP exposure | 0.11 ± 0.06 | −1.38 ± 0.06 |
| 082613; Sample W2, WBF2 Control | After exposure to 3% HP | −0.06 ± 0.10 | −1.54 ± 0.10 |
| 082613; Sample W5, WBF1-10ZO | After exposure to 3% HP | −0.06 ± 0.16 | −1.54 ± 0.16 |
| 082613; Sample S8, SBF1-20ZO | After exposure to 3% HP | 3.92 ± 2.41 | 2.43 ± 2.41 |
| 082613; Sample S9, SBF1-10ZO | After exposure to 3% HP | 0.10 ± 0.10 | −1.39 ± 0.10 |

*= "full kill"

Further testing was done on selected samples. The 100% solids samples #5, 7, 8, 9, 10, and 11 (Mylar control); the water-borne W3, W4, and W4a (W4 abraded with sandpaper); and solvent-based sample S8 were exposed to 3% HP for one hour, like before, and tested against EC. These results are shown in Table 7 below.

TABLE 7

Antimicrobial Activity of Selected Samples Against EC

| Sample versus EC | HP Exposure | Average Log Reduction Overnight | Average Log Reduction t = 0 |
|---|---|---|---|
| 083013; Sample 5, F1-10ZH | 1 hr. exposure to 3% HP | 0.13 ± 0.05 | −1.49 ± 0.05 |
| 083013; Sample 7, F1-20ZO | 1 hr. exposure to 3% HP | 6.78* ± 0.00 | 5.16* ± 0.00 |
| 083013; Sample 8, F2-20ZO | 1 hr. exposure to 3% HP | 6.78* ± 0.00 | 5.16* ± 0.00 |
| 083013; Sample 9, F1-15ZO | 1 hr. exposure to 3% HP | 6.78* ± 0.00 | 5.16* ± 0.00 |
| 083013; Sample 10, F2-15ZO | 1 hr. exposure to 3% HP | 6.78* ± 0.00 | 5.16* ± 0.00 |

TABLE 7-continued

Antimicrobial Activity of Selected Samples Against EC

| Sample versus EC | HP Exposure | Average Log Reduction Overnight | Average Log Reduction t = 0 |
|---|---|---|---|
| 082613; Sample 11, Blank Mylar Control | 1 hr. exposure to 3% HP | −0.11 ± 0.03 | −1.73 ± 0.03 |
| 083013; Sample S8, SBF1-20ZO | 1 hr. exposure to 3% HP | 6.78* ± 0.00 | 5.16* ± 0.00 |
| 083013; Sample WBF1-20ZO | 1 hr. exposure to 3% HP | 0.42 ± 0.46 | −1.20 ± 0.46 |
| 083013; Sample WB-F2-20ZO | 1 hr. exposure to 3% HP | 0.01 ± 0.14 | −1.61 ± 0.14 |
| 083013; Sample WB-F2-20ZO; with abrasion | 1 hr. exposure to 3% HP | −0.04 ± 0.06 | −1.66 ± 0.06 |

The water-borne (WB) samples of this example showed essentially zero efficacy. It will be seen in later examples that increasing the hydrophilic character of WB coatings will increase efficacy. The solvent-borne sample SBF 1-20ZO again showed high efficacy. All the 100%-solids UV samples (15 and 20% ZO) showed great efficacy. Uncoated Mylar exposed to HP did not show any efficacy.

Example 9

Water-Borne Coatings with Increased Hydrophilic Character

The water-borne self-crosslinking polyurethane dispersion based on Alberdingk U915 (as in Example 7b) was modified by adding 25% (by weight solids) of a hydrophilic acrylic binder dispersion Alberdingk AC2570 (Stock Formulation XR-NSF-WB-F3). The two dispersions were completely compatible and gave a clear "control" coating (0% ZnO).

XR-NSF-WB-F3 Self Crosslinking Formulation/Hydrophilic Co-Dispersion

| Component | Function | Weight % |
|---|---|---|
| IPA | Co-solvent | 0.99 |
| Alberdingk U915 | Water-borne SXL PUD 34% in water | 76.97 |
| AC2570 | Hydrophilic Acrylic Co-dispersion | 21.87 |
| Dynol 607 | Surface Active Agent | 0.17 |
| Total | | 100.0 |

The WB-F3 was then doped, separately, with 20% ZO and 30% ZO using Nanobyk 3840 ZO dispersion from Byk-Chemie. The formulation scheme was as shown in Table 8 below.

TABLE 8

WBF3-ZO Formulations.

| NanoZinc Solution | Amount Based on Binder Solids | % NV | PHR to be added | For 30 grams | Final % Solids | CW, 8R Wet: 18.3 gsm |
|---|---|---|---|---|---|---|
| NB3840 40% in water | 20 | 40 | 17.7 | 5.3 | 36.12 | 6.61 |
| NB3840 40% in water | 30 | 40 | 26.6 | 8.0 | 36.40 | 6.66 |

The dispersions were coated on SKC's SH41 PET (Mylar) substrate using a #8 Wire Rod. The dry coating weights (CW) were calculated as shown in Table 8 above. Both 20ZO and 30ZO gave excellent coatings on the PET substrate. The self-crosslinking polyurethane dispersion/acrylic combination formulation (WB-F3) was "physically dry" after drying the water off and continued to develop its physical property due to self-crosslinking. The following coatings were prepared by this method.
1) XR-NSF-WBF3 (Control)
2) WBF3-20ZO (WBF3 stock loaded with 20% Nano Zinc Oxide)
3) WBF3-30ZO (WBF3 stock loaded with 30% Nano Zinc Oxide)

Example 10

Solvent-Borne Coatings Based on Thermoplastic Polymers

Two different thermoplastic polymers were studied as solvent-borne coatings.
(a) Solvent-borne Coatings Based on High Molecular Weight Thermoplastic Polyvinylacetate (VINNAPAS® UW 4 FS): The resin was dissolved in methylethylketone at 10% solids to give a low viscosity liquid. It was further modified with a surface active wetting agent (Byk3440). This stock solution was XR-NSF-SB-F1D (SB-F1 for short). SB-F1D was then doped with the solvent-based ZO (Nanobyk 3841) to get 15% and 20% ZO loadings respectively as shown below in Table 9. The viscosity of the final solution was significantly lower than in Example 7 (with 30% solids).
(b) Solvent-borne Coatings Based on Low Molecular Weight Thermoplastic Polyvinylacetate (VINNAPAS® B60): The resin was dissolved in methylethylketone at 20% solids to give a low viscosity liquid. It was further modified with a surface active wetting agent (Byk3440). This stock solution was XR-NSF-SB-F3D (SB-F3D for short). SB-F3D was then doped with the solvent-based ZO (Nanobyk 3841) to get 15% and 20% ZO loadings respectively as shown below in Table 9. The viscosity of the final solution was similar to SB-F1D although the % solids was higher due to the lower molecular weight of the virgin polyvinylacetate.

TABLE 9

Formulations for the Solvent-Borne Systems

| Polyurethane Dispersion | NanoZinc Solution | % ZO based on total solids | PHR to be added | % Nanoparticle | % Resin Solution | PHR to be added | For 15 g | Final % Solids | CW, 8R Wet: 18.3 g/m |
|---|---|---|---|---|---|---|---|---|---|
| Vinnapas UVV4 20% | NB3840 40% in methoxypropylacetate | 15 | 17.65 | 40 | 10 | 4.4125 | 0.66 | 11.27 | 2.06 |
| XR-NSF-SB-F1D | NB3840 40% in methoxypropylacetate | 20 | 25 | 40 | 10 | 6.25 | 0.94 | 11.76 | 2.15 |
| Vinnapas UVV4 20% | NB3840 40% in methoxypropylacetate | 15 | 17.65 | 40 | 20 | 8.825 | 1.32 | 21.62 | 3.96 |
| XR-NSF-SB-F3D | NB3840 40% in methoxypropylacetate | 20 | 25 | 40 | 20 | 12.5 | 1.88 | 22.22 | 4.07 |

Using the above procedure, the following coatings were made up from the above solvent-borne solutions:

1) XR-NSF-SB-F1D (Control-0% ZnO)
2) SB-F1D-20ZO (SB-F1D stock loaded with 20% Nano Zinc Oxide)
3) SB-F1D-15ZO (SB-F1D stock loaded with 15% Nano Zinc Oxide)
4) XR-NSF-SB-F3D (Control-0% ZnO)
5) SB-F3D-20ZO (SB-F3D stock loaded with 20% Nano Zinc Oxide)
6) SB-F3D-15ZO (SB-F3D stock loaded with 15% Nano Zinc Oxide)

The solutions were coated on SKC's SH41 PET substrate using a #8 Wire Rod. The dry coating weights were calculated as shown in the Table 9 above. Each solvent-borne coating solution gave excellent coatings on the PET substrate. There were no rod marks visible, and the coatings were quite uniform. The solvent borne systems were physically dry after solvent removal (2 mins at 180 C) and assumed its final physical property immediately due to its high MW nature.

Example 11

Water-Borne Coatings With Increased Hydrophilic Character Prepared From a Physically Drying Polyurethane Dispersion This experiment outlines the preparation of water-borne coatings that incorporate a physically drying polyurethane dispersion rather than a self-crosslinking dispersion. The new formulation was designated XR-NSF-WB-F4 and comprised 36% of the hydrophilic acrylic polymer.

| XR-NSF-WB-F4 Self Crosslinking Formulation/Higher Hydrophilic Co-Dispersion | | |
|---|---|---|
| Component | Function | Weight % |
| Alberdingk U 915 | Water-borne SXL PUD 34% in water | 70.00 |
| AC2570 | Hydrophilic Acrylic Co-dispersion | 29.80 |
| Dynol 607 | Surface Active Agent | 0.17 |
| Total | | 100.0 |

Two different loadings of ZO were used—20% and 30%. The following samples were coated on SH41 polyester film from SKC, Inc using Rod#16:

1) WB-F4-20ZO (XR-NSF-WB-F4 stock loaded with 20% Nano Zinc Oxide)
2) WB-F4-30ZO (XR-NSF-WB-F4 stock loaded with 30% Nano Zinc Oxide)

The coating weights of each are shown in Table 10 below:

TABLE 10

XR-NSF-WB-F3 Zinc Oxide Formulations

| NanoZinc Solution | Amount Based on Binder Solids | % NV | PHR to be added | For 30 grams | Final % Solids | CW, 8R Wet: 18.3 gsm |
|---|---|---|---|---|---|---|
| NB3840 40% in water | 20 | 40 | 16.5 | 5.0 | 34.07 | 12.47 |
| NB3840 40% in water | 30 | 40 | 24.8 | 7.4 | 34.46 | 12.61 |

All coatings had excellent physical characteristics.

Example 12

Preparation of Higher Coating Weight Solvent-Borne Coatings

Two different thermoplastic polymers were studied as solvent-borne coatings.

(a) Solvent-borne Coatings Based on High Molecular Weight Thermoplastic Polyvinylacetate (VINNAPAS® UW 4 FS): The resin was dissolved in methylethylketone at 10% solids to give a low viscosity liquid. It was further modified with a surface active wetting agent (Byk3440). This stock solution was XR-NSF-SB-F1D (SB-F1 for short). SB-F1D was then doped with the solvent-based ZO (Nanobyk 3841) to get 15% and 20% ZO loadings respectively as shown below in Table 11. The viscosity of the final solution was significantly lower than before (with 30% solids).

(b) Solvent-borne Coatings Based on Low Molecular Weight Thermoplastic Polyvinylacetate (VINNAPAS® B60): The resin was dissolved in methylethylketone at 20% solids to give a low viscosity liquid. It was further modified with a surface active wetting agent (Byk3440). This stock solution was XR-NSF-SB-F3D (SB-F3D for short). SB-F3D was then doped with the solvent-based ZO (Nanobyk 3841) to get 15% and 20% ZO loadings respectively as shown below in Table 11. The viscosity of the final solution was similar to SB-F1D although the % solids was higher due to the lower molecular weight of the virgin polyvinylacetate.

TABLE 11

Formulatory Schemes for the Solvent-Borne Systems

| Polyurethane Dispersion | NanoZinc Solution | % ZO based on total solids | PHR to be added | % Nanoparticle | % Resin Solution | PHR to be added | For 15 g | Final % Solids | CW, 16R Wet: 18.3 g/m |
|---|---|---|---|---|---|---|---|---|---|
| Vinnapas UVV4 20% XR-NSF-SB-F1D | NB3840 40% in methoxypropylacetate | 20 | 25 | 40 | 10 | 6.25 | 0.94 | 11.76 | 4.31 |
| Vinnapas UVV4 20% XR-NSF-SB-F3D | NB3840 40% in methoxypropylacetate | 20 | 25 | 40 | 20 | 12.5 | 1.88 | 22.22 | 8.13 |

Using the above procedure, the following coatings were made up from the above solvent-borne solutions:

1) SB-F1D-20ZO (SB-F1D stock loaded with 20% Nano Zinc Oxide)
2) SB-F3D-20ZO (SB-F3D stock loaded with 20% Nano Zinc Oxide)

The solutions were coated on SKC's SH41 PET substrate using a #16 Wire Rod. The dry coating weights were calculated as shown in the Table 11 above. Each solvent-borne coating solution gave excellent coatings on the PET substrate. There were no rod marks this time around and the coatings were quite uniform. The solvent borne systems were physically dry after solvent removal (2 mins at 180 C) and assumed its final physical property immediately due to its high molecular weight nature.

Example 13

Antimicrobial Activity of UV Curable Coatings of Examples 5 and 7

The UV curable coatings of Example 5 (Table 1) and the solvent-borne coatings of Example 7 (Tables 4 and 5) were exposed to hydrogen peroxide and tested against *E. coli* (EC), and *S. aureus* (SA). Note that EC is generally a more difficult to kill organism than SA. Data for these previously-described coatings is summarized in Tables 12 and 13 below.

Although there is some variation in data from the previous tests, some general trends are apparent. Most samples performed very well after 10% HP exposure. At lower concentrations (1% and 3%), the solvent-borne coating formulations did particularly well.

TABLE 12

Antimicrobial Activity of Coatings Against *S. aureus*

| | Average Log Reduction t = 0 | | |
|---|---|---|---|
| Sample versus SA | HP Exposure 0% | HP Exposure 1% | HP Exposure 10% |
| Sample 1, XR-NSF-UV-F1 Control | | | 5.24* ± 0.00 |

TABLE 12-continued

Antimicrobial Activity of Coatings Against *S. aureus*

| | Average Log Reduction t = 0 | | |
|---|---|---|---|
| Sample versus SA | HP Exposure 0% | HP Exposure 1% | HP Exposure 10% |
| Sample 2, UV-F2 Control | 0.97 ± 0.08 | 0.64 ± 0.25 | 5.24* ± 0.00 |
| Sample 3, F1-15ZP | | | 5.24* ± 0.00 |
| Sample 4, F2-15ZP | | | 5.24* ± 0.00 |
| Sample 5, F1-10ZH | | | 5.24* ± 0.00 |
| Sample 6, F2-10ZH | | | 5.24* ± 0.00 |
| Sample 7, F1-20ZO | | | 5.24* ± 0.00 |
| Sample 8, F2-20ZO | 1.42 ± 0.16 | 1.72 ± 0.30 | 5.24* ± 0.00 |
| Sample 9, F1-15ZO | | | 5.24* ± 0.00 |
| Sample 10, F2-15ZO | 1.03 ± 0.05 | 1.80 ± 0.00 | 5.24* ± 0.00 |
| Sample 11, Blank Mylar Control | −0.13 ± 0.01 | 0.06 ± 0.24 | 5.24* ± 0.00 |
| Sample S8, SBF1-20ZO | 0.64 ± 0.03 | 3.91 ± 1.74 | |
| Sample S9, SBF1-10ZO | 0.42 ± 0.01 | 1.43 ± 0.22 | |

TABLE 13

Antimicrobial Activity of Coatings Against *E. coli*

| Sample versus EC | Average Log Reduction t = 0 | | | |
|---|---|---|---|---|
| | HP Exposure 0% | HP Exposure 1% | HP Exposure 3% | HP Exposure 10% |
| Sample 1, XR-NSF-UV-F1 Control | | | | −1.17 |
| Sample 2, UV-F2 Control | −1.41 ± 0.06 | | −1.11 ± 0.15 | −1.24 |
| Sample 3, F1-15ZP | | | | −1.21 ± 0.06 |
| Sample 4, F2-15ZP | | | | −1.11 ± 0.06 |
| Sample 5, F1-10ZH | | | −1.49 ± 0.05 | 5.18* ± 0.00 |
| Sample 6, F2-10ZH | −1.67 ± 0.36 | | −1.43 ± 0.41 | 5.18* ± 0.00 |
| Sample 7, F1-20ZO | | −0.74 ± 0.08 | 5.16* ± 0.00 | 5.18* ± 0.00 |
| Sample 8, F2-20ZO | | −1.11 ± 0.02 | 5.16* ± 0.00 | 5.18* ± 0.00 |
| Sample 9, F1-15ZO | | −1.23 ± 0.13 | 5.16* ± 0.00 | 5.18* ± 0.00 |
| Sample 10, F2-15ZO | −1.67 ± 0.15 | −1.34 ± 0.05 | 5.16* ± 0.00, 5.14* ± 0.00 | 5.18* ± 0.00 |
| Sample 11, Blank Mylar Control | −1.69 ± 0.17, −0.70 ± 1.26 | 0.20 ± 2.49 | −1.73 ± 0.03, 0.53 ± 0.66 | |
| Sample S8, SBF1-20ZO | | −1.42 ± 0.07 | 5.16* ± 0.00, 2.43 ± 2.41 | |
| Sample S9, SBF1-10ZO | | −1.47 ± 0.09 | −1.39 ± 0.10 | |
| Sample W2, WBF2 Control | | | −1.54 ± 0.10 | |
| Sample W3, WBF1-20ZO | −1.38 ± 0.06 | | −1.20 ± 0.46, −1.42 ± 0.01 | |
| Sample W4, WB-F2-20ZO | | | −1.61 ± 0.14 | |
| Sample W4a, WB-F2-20ZO; abraded | | | −1.66 ± 0.06 | |
| Sample W5, WBF1-10ZO | | | −1.54 ± 0.16 | |

Example 14

Further Testing of Solvent-Borne Coatings

The solvent-borne (SB) coating formulations were further tested. Sample S8 (SBF1-20ZO) was selected and a time-study for exposure to 3% HP was done. Samples were then tested against EC. We found that even after only 3 minutes exposure to HP, significant antimicrobial efficacy was apparent. Samples were tested after drying for at least 24 hours after HP exposure. See Table 14 for data. Sample S8 was also exposed to a commercial HP-based cleaning product (Clorox) containing 1.4% HP, but no efficacy was seen after simple wiping with the product.

TABLE 14

Antimicrobial Activity of Solvent-Borne Coating S8 Against *E. coli*

| Sample versus EC | HP Exposure | Average Log Reduction Overnight | Average Log Reduction t = 0 |
|---|---|---|---|
| 091213; Sample 8, F2-20ZO; A | 1 min soak in 3% HP | 0.05 ± 0.03 | −1.35 ± 0.03 |
| 091213; Sample 8, F2-20ZO; B | 5 min soak in 3% HP | 3.55 ± 4.48 | 2.15 ± 4.48 |
| 091213; Sample 8, F2-20ZO; C | 15 min soak in 3% HP | 6.72* ± 0.00 | 5.32* ± 0.00 |
| 091213; Sample 8, F2-20ZO; D | 30 min soak in 3% HP | 6.72* ± 0.00 | 5.32* ± 0.00 |
| 091113; C1, Solvent coating, 0% Zn | 30 min soak in 3% HP | 0.06 ± 0.03 | −1.34 ± 0.03 |
| 091213; Sample 8, F2-20ZO; E | wiped with 3% HP paper towel | −0.04 ± 0.05 | −1.34 ± 0.05 |
| 091213; Sample 8, F2-20ZO; F | wiped with Lysol cleaner paper towel | −0.10 ± 0.13 | −1.44 ± 0.13 |
| 091113; C2, Solvent coating, 0% Zn | wiped with Lysol cleaner paper towel | −0.22 ± 0.12 | −1.61 ± 0.12 |
| 091113; C0, Solvent coating, 0% Zn | No HP exposure | 0.03 ± 0.04 | −1.37 ± 0.04 |

Example 15

Incorporation of ZnO into Commercial Floor Wax Composition

Commercial ZnO powder (micron sized, Aldrich Chemical) was incorporated into an aqueous-based floor wax composition (Stampede) at loadings of 20% and 50% (dried solids basis). These were tested after exposure to 3% HP for 30 minutes against EC and SA, and allowed to dry at least 24 hours. The 50% sample, and also previous sample S8 were also exposed to Clorox HP cleaner for 5 minutes, then wiped and allowed to air dry overnight. All samples showed excellent efficacy against EC and SA in the standard ASTM agar slurry test. See Tables 15 and 16.

TABLE 15

Floor Wax Composition Comprising Coating Compositions

| Sample versus EC N = 2 | HP Exposure | Average Log Reduction Overnight | Average Log Reduction t = 0 |
|---|---|---|---|
| 091813; Floor wax coating, 0% ZnO | 30 min soak in 3% HP | −0.03 ± 0.03 | −1.78 ± 0.03 |
| 091813; Floor wax coating, 20% ZnO | 30 min soak in 3% HP | 6.87* ± 0.00 | 5.13* ± 0.00 |
| 091813; Floor wax coating, 50% ZnO | 30 min soak in 3% HP | 6.87* ± 0.00 | 5.13* ± 0.00 |
| 091813; Sample 8, F2-20ZO | Clorox HP cleaner | 6.87* ± 0.00 | 5.13* ± 0.00 |
| 091813; Wax coating, 50% ZnO | Clorox HP cleaner | 6.87* ± 0.00 | 5.13* ± 0.00 |

TABLE 16

Wax Composition Comprising coating Composition Treated with Cleaner

| Sample versus SA N = 2 | HP Exposure | Average Log Reduction Overnight | Average Log Reduction t = 0 |
|---|---|---|---|
| 091813; Sample 8, F2-20ZO | Clorox HP cleaner application | 5.71* ± 0.00 | 5.29* ± 0.00 |
| 091813; Wax coating, 50% ZnO | Clorox HP cleaner application | 5.71* ± 0.00 | 5.29* ± 0.00 |

Example 16

Addition of Zinc Oxide to Latex Paints

Valspar Bare Wood Primer was selected as a carrier for inclusion of ZnO particles since it was previously tested and showed zero inherent antimicrobial activity. Samples were prepared with "high" and "low" ZnO content (approximately 15 and 30% ZnO solids basis was added—Sample # 104A and 104B, respectively). Commercial ZnO powder (micron sized, Aldrich Chemical) was used. Samples of these coatings were exposed to 3% and 10% HP for one hour. Results are shown in Table 17. Both samples exposed to 10% HP showed high antimicrobial efficacy; however, a control sample (0% ZnO) also showed good efficacy after exposure to 10% HP. With 3% HP, both samples showed slight to moderate efficacy which was higher than that of the 0% control.

TABLE 17

Antimicrobial Activity Against *E. coli* of Latex Paint coatings exposed to Zinc Oxide

| Sample versus EC | HP Exposure | Average Log Reduction Overnight | Average Log Reduction t = 0 |
|---|---|---|---|
| 100313; Stay Fresh 104A ZnO; A3 | After exposure to 3% HP | 2.17 ± 0.76 | 0.61 ± 0.76 |
| 100313; Stay Fresh 104B ZnO; B3 | After exposure to 3% HP | 1.57 ± 0.40 | 0.01 ± 0.40 |
| 100313; Control; C3 | After exposure to 3% HP | 0.45 ± 0.03 | −1.11 ± 0.03 |
| 100313; Stay Fresh 104A ZnO; A10 | After exposure to 10% HP | 6.71* ± 0.00 | 5.15* ± 0.00 |
| 100313; Stay Fresh 104B ZnO; B10 | After exposure to 10% HP | 6.71* ± 0.00 | 5.15* ± 0.00 |
| 100313; Control; C10 | After exposure to 10% HP | 6.71* ± 0.00 | 5.15* ± 0.00 |

Example 17

Coating Compositions Having Higher Hydrophilic Character

Formulations having even higher hydrophilic character than the previously described formulations of Examples 9 and 11 were prepared in a similar manner. The water-borne coating compositions were made at 20 and 30% nano-ZnO (samples WBF4-30ZO and WBF4-20ZO). The newer solvent-borne coating samples were prepared similar to the previous batch, but were made from more diluted coating solutions (Samples SBF1D-20ZO and SBF3D-30ZO). These were exposed to 3% HP for 1 hour, and tested against EC after drying for one day. Results are presented below in Table 18, and all the water-borne and solvent-borne coating samples showed high efficacy. The exposure of sample 104A (Example 16, above) to 3% HP was also repeated, and the same moderate efficacy was observed.

The HP-exposed samples tested in Table 18 were stored for one week, then retested against EC. Results are shown in Table 19. After storage for a week, the WB samples (20 and 30%) both retained full efficacy. However, the SB samples lost all efficacy. The 104A sample lost some efficacy, but was not very high to start with. This is the first data to conclusively show that the efficacy imparted by HP is not permanent. We had been working under the assumption that the residual antimicrobial efficacy seen after samples are exposed to HP was indefinite. We have determined that the duration of efficacy can range from 24 hours to at least one week, depending on formulation. In most of the early testing described above we did not carefully monitor the time elapsed between HP-exposure and antimicrobial testing; however, in all cases it was at least 24 hours.

TABLE 18

Antimicrobial Activity of Coating Samples of Example 20

| Samples dried 24 hours Sample versus EC | HP Exposure | Average Log Reduction Overnight | Average Log Reduction t = 0 |
|---|---|---|---|
| 101513; 104A latex paint w/ZnO added | Exposure to 3% HP for 60 min | 1.72 ± 0.14 | −0.37 ± 0.14 |
| 101513; W30 = WB F4-30ZO | Exposure to 3% HP for 60 min | 6.78* ± 0.00 | 4.70* ± 0.00 |
| 101513; W20 = WB F4-20ZO | Exposure to 3% HP for 60 min | 6.78* ± 0.00 | 4.70* ± 0.00 |
| 101513; S1 = SBF1D-20ZO | Exposure to 3% HP for 60 min | 6.78* ± 0.00 | 4.70* ± 0.00 |
| 101513; S3 = SBF3D-20ZO | Exposure to 3% HP for 60 min | 6.78* ± 0.00 | 4.70* ± 0.00 |

TABLE 19

Antimicrobial Activity of Coating Samples of Example 20 After 1-Week Storage

| Stored 1 Week Before Testing Sample versus EC | HP Exposure | Average Log Reduction Overnight | Average Log Reduction t = 0 |
|---|---|---|---|
| 101513; 109A latex paint w/ZnO added | Exposure to 3% HP for 60 min | 1.24 ± 0.07 | −0.46 ± 0.07 |
| 101513; W30 = WB F4-30ZO | Exposure to 3% HP for 60 min | 6.93* ± 0.00 | 5.23* ± 0.00 |
| 101513; W20 = WB F4-20ZO | Exposure to 3% HP for 60 min | 6.93* ± 0.00 | 5.23* ± 0.00 |
| 101513; S1 = SBF1D-20ZO | Exposure to 3% HP for 60 min | 0.31 ± 0.15 | −1.39 ± 0.15 |
| 101513; S3 = SBF3D-20ZO | Exposure to 3% HP for 60 min | 0.18 ± 0.07 | −1.52 ± 0.07 |

As a result of the time-decay observations observed, we repeated antimicrobial testing on several HP-exposed samples that had previous given good efficacy results. We found that most of these lost efficacy after being stored for periods ranging from 3 weeks to 2 months. It should be pointed out that even a 1-week duration for residual antimicrobial efficacy is significantly better than the ~5-minute efficacy after drying offered by non-ZnO surfaces after exposure to HP.

In addition, sample WB F4D (20% ZnO) was tested for antimicrobial efficacy against other organisms after exposure to 10% HP for one hour, followed by drying for 24 hours. The organisms tested included *Staph. Aureus* (SA), Methacillin-resistant *Staph. Aureus* (MRSA), *Klebsiella Pneumonia* (KP), and *Enterococcus Faecium* (EFm). All samples exhibited high antimicrobial efficacy (full kill) against these organisms, as shown in Table 20 below.

TABLE 20

Antimicrobial Activity of Water-Borne Coatings Against Various Organisms

| Organism | Log Reduction (t = 0) |
|---|---|
| EFm | 5.20* ± 0.00 |
| SA | 5.19* ± 0.00 |
| MRSA | 4.93* ± 0.00 |
| KP | 5.19* ± 0.00 |

*indicates full kill

Example 18

Timed Exposure of Water-Borne Coatings to Hydrogen Peroxide

Water-borne coating formulations F4 (of Example 17) were exposed to 3% HP for either 5, 15, or 30 minutes, or treated with Clorox HP spray (1.4% HP) for 5 minutes. Samples were tested against EC after drying for 1, 3, and 7 days. Results are shown in Table 21. Efficacy at 1 and 3 days drying generally increased with increasing HP exposure time. For the 30% ZnO HP-exposed samples, efficacy diminished only slightly (if at all) between day 1 and day 3 or Day 7. The 20% ZO sample at 15 minute exposure was also run separately (both exposure and efficacy) in another series of assays and achieved similar results to the first set of testing. The 20% ZnO sample exposed to Clorox HP cleaner showed very high efficacy after 1 day, but no efficacy after 3 or 7 days dry storage. The 30% ZnO sample showed no efficacy after exposure to Clorox cleaner.

TABLE 21

Antimicrobial Activity of Water-Borne Coating after Timed Exposure

| Sample versus EC | HP Exposure | Average Log Reduction 1 day (t = 0) | Average Log Reduction 3 days (t = 0) | Average Log Reduction 7 days (t = 0) |
|---|---|---|---|---|
| WB F4D 20% ZO | 3% HP for 5 min | 1.89 ± 0.27 | 1.92 ± 0.22 | — |
| WB F4D 20% ZO | 3% HP for 15 min | 2.34 ± 0.08 | 2.06 ± 0.33 | — |
| WB F4D 20% ZO** | 3% HP for 15 min | 4.07 ± 0.34 | 2.12 ± 0.24 | 1.27 ± 0.13 |
| WB F4D 20% ZO | 3% HP for 30 min | 4.65 ± 1.04 | 2.81 ± 0.49 | — |
| WBF4D 20% ZO | Clorox HP | 5.39* ± 0.00 | −1.60 ± 0.12 | — |
| WB F4D 30% ZO | 3% HP for 5 min | 2.61 ± 0.07 | 1.33 ± 0.04 | 2.68 ± 0.07 |
| WB F4D 30% ZO | 3% HP for 15 min | 1.88 ± 0.25 | 1.73 ± 0.05 | 1.89 ± 0.54 |
| WB F4D 30% ZO | 3% HP for 30 min | 5.39* ± 0.00 | 4.50 ± 1.13 | 5.18* ± 0.00 |
| WB F4D 30% ZO | Clorox HP | −0.03 ± 0.16 | −1.41 ± 0.07 | — |

*indicates full kill

**additional assay performed for this formulation

Example 19

Effect of pH on Antimicrobial Activity of Water-Borne Coatings

Samples of WB-F4 were treated with 3% HP for 15 minutes at various pH conditions, as shown in Table 22 below. Within the uncertainty of the measurements, there were not any obvious large differences between the various pH conditions after 1 day or 7 days of drying. The high pH HP solution showed some decomposition, as evidenced by gas bubble formation. Note that the pH=3.75 is the "normal" (uncorrected) pH of the HP solution. Addition of 5% ethanol did not improve efficacy. The general loss of efficacy between 1 and 7 days for all samples is similar in magnitude to that described above.

TABLE 22

Antimicrobial Activity of Water-Borne Coating at Various pH

| Sample versus EC | HP Exposure | Average Log Reduction 1 day (t = 0) | Average Log Reduction 7 days (t = 0) |
|---|---|---|---|
| WBF4-30% ZO; pH 3.75 | 3% HP for 15 min | 4.73 ± 0.71 | 2.03 ± 1.02 |
| WBF4-30% ZO; pH 1.65 | 3% HP for 15 min | 5.23* ± 0.00 | 0.66 ± 0.92 |
| WBF4-30% ZO;, pH 8.85 | 3% HP for 15 min | 3.93 ± 0.00 | 1.18 ± 0.51 |
| WBF4-30% ZO; pH 3.75 + 5% EtOH | 3% HP for 15 min | 3.50 ± 0.17 | 1.98 ± 0.12 |

*indicates full kill

Example 20

Additional Studies with Water-Borne Coatings of Example 9

WB F3 samples were made at 20% nano-ZnO content. Samples were exposed to 3% HP for 30 minutes, and tested after 24 hours of drying. Time-kill profile: Note that all of the testing described in prior examples above has utilized an overnight (18-24 hour) bacterial contact (incubation) time. That is, samples are inoculated with bacteria and the residual viable bacteria are enumerated after 18-24 hours of exposure to the antimicrobial surface. We performed a time-kill study by looking at various contact times ranging from 5 minutes to overnight. Data was collected for EC and also for MRSA (methicillin-resistant Staph. aureus). This data is presented in the Tables 23 and 24, below.

TABLE 23

Antimicrobial Activity of Water-Borne Coatings versus E. Coli

| Sample versus EC | 3% HP - 15 min 24 hour dry Incubation Time | Average Log Reduction Overnight | Average Log Reduction t = 0 |
|---|---|---|---|
| WBF3-20 ZO | 5 min | 1.06 ± 0.14 | 0.01 ± 0.14 |
| WBF3-20 ZO | 10 min | 0.95 ± 0.08 | −0.09 ± 0.08 |
| WBF3-20 ZO | 30 min | 0.99 ± 0.04 | −0.05 ± 0.04 |
| WBF3-20 ZO | 1 hr | −0.19 ± 0.03 | −1.23 ± 0.03 |
| WBF3-20 ZO | 2 hr | 0.90 ± 0.06 | −0.14 ± 0.06 |
| WBF3-20 ZO | 4 hr | 1.10 ± 0.03 | 0.05 ± 0.03 |
| 111213; WBF3-20 ZO | Overnight | 3.42 ± 4.79 | 1.76 ± 4.79 |

TABLE 24

Antimicrobial Activity of Water-Borne Coatings versus methicillin-resistant Staph. Aureus (MRSA).

| Sample versus MRSA | 3% HP - 30 min 24 hour dry Incubation Time | Average Log Reduction | Average Log Reduction |
|---|---|---|---|
| WBF3-20 ZO | 5 min | 0.17 ± 0.03 | 0.02 ± 0.03 |
| WBF3-20 ZO | 10 min | 0.16 ± 0.02 | 0.00 ± 0.02 |
| WBF3-20 ZO | 30 min | 0.30 ± 0.02 | 0.14 ± 0.02 |
| WBF3-20 ZO | 1 hr | 0.53 ± 0.21 | 0.38 ± 0.21 |
| WBF3-20 ZO | 2 hr | 0.87 ± 0.14 | 0.72 ± 0.14 |
| WBF3-20 ZO | 4 hr | 2.81 ± 0.05 | 2.66 ± 0.05 |
| WBF3-20 ZO | Overnight | 5.46* ± 0.00 | 4.97* ± 0.00 |

*indicates full kill

Overnight efficacy was excellent against MRSA, and good against EC. Significant efficacy is exhibited against MRSA after 4 hours.

Example 21

Antimicrobial Activity of Example 9 Water-Borne Coatings Activated with Peridox A sample of Peridox RTU™, a commercial hydrogen peroxide-based cleaner, was obtained from the manufacturer (BioMed Protect). The Peridox cleaner contains 4.4% HP and 0.23% peroxyacetic acid as the active ingredients. Samples of WB F3 of Example 9 coating were exposed to Peridox for various time periods. Significant efficacy was observed for the 15 minute exposure (see Table 25). See also data in Table 26 of the next example.

TABLE 25

Antimicrobial Activity of Water-Borne Coatings versus E. coli

| Sample versus EC | Dried 24 hours HP Exposure | Average Log Reduction Overnight | Average Log Reduction t = 0 |
|---|---|---|---|
| WB F3 20ZO; | 2 min Peridox | −0.25 ± 0.00 | −1.77 ± 0.00 |
| WB F3 20ZO; | 5 min Peridox | −0.21 ± 0.03 | −1.74 ± 0.03 |
| WB F3 20ZO; | 15 min Peridox | 3.25 ± 4.87 | 1.73 ± 4.87 |

Example 22

Antimicrobial Activity of Water-Borne Coatings Containing Micron-Sized Zinc Oxide Water-Borne Coating samples, similar to the WB-F3 and WB-F4 formulations of Examples 1 and 13, were prepared using similar polymer formulations. However, micron sized ZnO (commercially available from Aldrich) was used instead of nano-ZnO used previously. Two formulations were made using the procedures of Examples 11 and 13. Sample 1120A was made using 21 g Alberdingk U915, 15 g H2O, and 2.6 g ZnO (Dry), which was then homogenized, followed by addition of 10 g Alberdingk AC2570 and mixing by hand. Sample 1120B was made using 21 g Alberdingk U915, 10 g H2O, and 2.6 g ZnO (Dry), which was then homogenized, followed by addition of 15 g Alberdingk AC2570 and mixing by hand. In addition, a control sample (0% ZnO) was made. All were coated onto Mylar sheets. As shown Table 26 below, the samples with micron ZnO showed excellent efficacy after being exposed to 3% HP for 1 hour, or 10% HP for various times, or Peridox or Clorox HP cleaner for 5 minutes, followed by 24 hours drying.

TABLE 26

Antimicrobial Activity of Water-Borne Coatings Comprising
Micron-sized Zinc Oxide versus *E. coli*

| Sample versus EC | Dried 24 hours After HP exposure | Average Log Reduction Overnight | Average Log Reduction t = 0 |
|---|---|---|---|
| 1120A, 20% ZnO | 1 hr, 3% HP | 6.70* ± 0.00 | 5.17* ± 0.00 |
| 1120B, 20% ZnO | 1 hr, 3% HP | 6.70* ± 0.00 | 5.17* ± 0.00 |
| 1120C, Control | 1 hr, 3% HP | 0.51 ± 0.10 | −1.01 ± 0.10 |
| 1120B, 20% ZnO | 5 min, 10% HP | 6.83* +/− 0.00 | 5.02* +/− 0.00 |
| 1120B, 20% ZnO | 10 min, 5% HP | 6.83* +/− 0.00 | 5.02* +/− 0.00 |
| 1120B, 20% ZnO | 1 hr, 10% HP | 6.83* +/− 0.00 | 5.02* +/− 0.00 |
| 1120B, 20% ZnO | 5 min, Clorox HP | 3.73 +/− 0.21 | 1.92 +/− 0.00 |
| 1120B, 20% ZnO | 5 min, Peridox HP | 6.83* +/− 0.00 | 5.02* +/− 0.00 |

*Indicates "full kill"

The above samples were stored for an additional 17 days, and the antimicrobial efficacy was reevaluated. Results are shown in Table 27.

TABLE 27

Antimicrobial Activity After 18-Day Drying Time

| Sample versus EC | Dried 18 Days HP Exposure | Average Log Reduction Overnight | Average Log Reduction t = 0 |
|---|---|---|---|
| 11201A, 20% ZnO | 18 day shelf-life | 1.31 ± 0.34 | −0.31 ± 0.34 |
| 1120B, 20% ZnO | 18 day shelf-life | 6.85* ± 0.00 | 5.23* ± 0.00 |

Example 23

Commercial Floor Wax Compositions

Samples based on a commercial acrylic floor-wax product (STAMPEDE) containing 10% and 20% of nano-ZnO were prepared and tested after exposure to 3% HP for 15 minute. Zero efficacy against EC was found. In a previous report we showed that 20% of micron-sized ZnO in a similar coating based on STAMPEDE showed good antimicrobial efficacy; however, this was after 30 minutes (rather than 15 minutes) exposure to 3% HP. This indicates that larger (micron) sized ZnO particles may give higher antimicrobial efficacy than nano ZnO particles when incorporated into coatings, followed by exposure to HP. However, the coatings made from micron-sized ZnO do not have the optical transparency exhibited by those made with nano ZnO.

Example 24

Treatment of Textiles

A coatings formulation chosen from those described in the above examples is used to treat a textile article, which may comprise cotton, rayon, polyester, nylon, acrylic or other material. The treatment may consist of wetting said textile with the coating formulation by spraying, dipping, padding or other means, followed by removal of excess coating liquid by means familiar to one skilled in the art, followed by drying of the treated article. Said coating formulation may be diluted with solvent or water prior to treating the textile. The dried textile will have ZnO particles immobilized on or in the textile. The ZnO particles can be activated to become antimicrobial by exposure to HP solution, such as during laundering.

Example 25

Inclusion of HP into Coating Formulation

Hydrogen Peroxide may be added to any coating formulation described in the above examples, particularly the aqueous-based systems. In this manner, the dried coatings will have antimicrobial efficacy even before subsequent exposure of the dried surface to HP solution. A preferred amount of HP is at least 1% by weight of the dried coating.

Having generally described this invention, those skilled in the art will appreciate that the present invention contemplates the embodiments of this invention as defined in the following claims, and equivalents thereof. However, those skilled in the art will appreciate that the scope of this invention should be measured by the claims appended hereto, and not merely by the specific embodiments exemplified herein. Those skilled in the art will also appreciate that more sophisticated technological advances will likely appear subsequent to the filing of this document with the Patent Office. To the extent that these later developed improvements embody the operative principles at the heart of the present disclosure, those improvements are likewise considered to come within the ambit of the following claims.

The invention claimed is:

1. A method of enhancing and regenerating durable antimicrobial activity of the surface of an article, wherein said method comprises the steps in sequence of:
   a. providing, on the surface of an article on which durable antimicrobial activity is desired, a polymer doped with a metal derivative,
   b. exposing the polymer doped with a metal derivative to a source of aqueous hydrogen peroxide for a time sufficient to permit an antimicrobially-enhancing amount of hydrogen peroxide to be sequestered thereon, and thereafter,
   c. removing the source of aqueous hydrogen peroxide,
   wherein said metal derivative comprises 1% to 50% (w/w) of the weight of the doped polymer, wherein said metal derivative is a hydroxide, an oxide, or a peroxide of a metal selected from the group consisting of zinc, magnesium, titanium, and zirconium,
   wherein the water absorbency of said polymer is between 0.5% and 20% (w/w), wherein said polymer doped with said metal derivative has been determined to be capable of sequestering hydrogen peroxide when exposed to said source of aqueous hydrogen peroxide;
   whereby said antimicrobial activity, when tested using ASTM Standard Method E2180 at least 24 hours after said removal of the source of hydrogen peroxide, provides at least a 3-log reduction of viable *Escherichia coli* bacteria greater than that of a corresponding surface of said polymer doped with said metal derivative which has not been exposed to hydrogen peroxide.

2. The method of claim 1, wherein determination of the capability of sequestering hydrogen peroxide by said polymer doped with said metal derivative further comprises, after step c, the step of;
   conducting an assay to determine the level of sequestered hydrogen peroxide of said polymer doped with said metal derivative.

3. The method of claim 2, wherein said assay is a titration test or a colorimetric spot test.

4. The method of claim 2, wherein said article is selected from the group consisting of medical implants; medical instruments or devices; hospital equipment; bed rails; table tops; bedpans; i.v. stands; lamp handles; blood pressure cuffs; dental equipment; surgical instruments; orthopedic devices; hot/cold packs; wheelchair cushions; doorknobs; bathroom fixtures; food preparation surfaces; equipment touch-screens; floor waxes; paints; inks; clear coats; varnish; kitchen equipment and tables in restaurants, schools, and other institutions; home appliances; and seats, armrests, railings, and tray tables for airlines and other public transportation.

5. The method of claim 1, wherein said metal derivative is selected from the group consisting of zinc hydroxide, zinc peroxide, zinc oxide, zinc oxide nanoparticles, and zinc oxide micron particles.

6. The method of claim 1, wherein said metal derivative is selected from the group consisting of zinc oxide nanoparticles and zinc oxide micron particles.

7. The method of claim 1, wherein said metal derivative comprises 10% to 30% (w/w) of the weight of the doped polymer.

8. The method of claim 1, where said polymer is selected from the group consisting of polyacrylonitrile, acrylonitrile butadiene styrene (ABS) polymer, acrylic (PMMA), celluloid, cellulose acetate, ethylene-vinyl acetate (EVA), ethylene vinyl alcohol (EVOH), fluoropolymers (PTFE, FEP, PFA, CTFE, ECTFE, ETFE), ionomers, acrylic/PVC alloy, liquid crystal polymer (LCP), polyacetal (POM or Acetal), polyacrylates (acrylic), polyacrylonitrile (PAN or acrylonitrile), polyamide (PA or Nylon), polyamide-imide (PAI), polyaryletherketone (PAEK or Ketone), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetheretherketone (PEEK), polyetherketoneketone (PEKK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC); styrene-acrylonitrile (SAN), silicone polymers, thermoplastics, thermosets, elastomers; and copolymers, blends, and mixtures thereof.

9. The method of claim 1, wherein said polymer is selected from the group of polyurethanes, polyacrylates, and polyvinyl acetate.

10. The method of claim 1, wherein the doped polymer is a mixture that further comprises a hydrophilic acrylic polymer.

11. The method of claim 1, wherein said source of aqueous hydrogen peroxide has a concentration of hydrogen peroxide between 0.5% and 10%.

12. The method of claim 1, wherein said source of aqueous hydrogen peroxide has a concentration of hydrogen peroxide between 1% and 5%.

13. The method of claim 1, wherein said source of aqueous hydrogen peroxide is a commercial cleaner containing at least 0.5% hydrogen peroxide.

14. The method of claim 1, wherein the exposure time of step b is 1 minute to 30 minutes.

15. The method of claim 1, wherein said article is selected from the group consisting of medical implants; medical instruments or devices; hospital equipment; bed rails; table tops; bedpans; i.v. stands; lamp handles; blood pressure cuffs; dental equipment; surgical instruments; orthopedic devices; hot/cold packs; wheelchair cushions; doorknobs; bathroom fixtures; food preparation surfaces; equipment touch-screens; floor waxes; paints; inks; clear coats; varnish; kitchen equipment and tables in restaurants, schools, and other institutions; home appliances; and seats, armrests, railings, and tray tables for airlines and other public transportation.

16. A regenerable antimicrobial coating comprising,
a. a metal derivative, wherein said metal derivative is a hydroxide, an oxide, or a peroxide of a metal selected from the group consisting of zinc, magnesium, titanium, and zirconium,
b. a polymer, wherein said polymer is doped with 1% to 50% (w/w) of said metal derivative,
c. sequestered hydrogen peroxide,
wherein the water absorbency of said polymer is between 0.5% and 20% (w/w), wherein said polymer doped with said metal derivative has been determined to be capable of sequestering hydrogen peroxide when exposed to said source of aqueous hydrogen peroxide; wherein the antimicrobial activity of said doped polymer can be regenerated on subsequent exposure to aqueous hydrogen peroxide,
whereby said antimicrobial coating, when tested using ASTM Standard Method E2180 at least 24 hours after preparation, provides at least a 3-log reduction of viable *Escherichia coli* bacteria greater than that of a corresponding coating which has not been exposed to hydrogen peroxide.

17. The regenerable antimicrobial coating of claim 16, wherein said polymer is selected from the group consisting of polyacrylonitrile, acrylonitrile butadiene styrene (ABS) polymer, acrylic (PMMA), celluloid, cellulose acetate, ethylene-vinyl acetate (EVA), ethylene vinyl alcohol (EVOH), fluoropolymers (PTFE, FEP, PFA, CTFE, ECTFE, ETFE), ionomers, acrylic/PVC alloy, liquid crystal polymer (LCP), polyacetal (POM or Acetal), polyacrylates (acrylic), polyacrylonitrile (PAN or acrylonitrile), polyamide (PA or Nylon), polyamide-imide (PAI), polyaryletherketone (PAEK or Ketone), polybutacliene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetheretherketone (PEEK), polyetherketoneketone (PEKK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC); styrene-acrylonitrile (SAN), silicone polymers, thermoplastics, thermosets, elastomers; and copolymers, blends, and mixtures thereof.

18. The regenerable antimicrobial coating of claim 16, wherein said polymer is selected from the group of polyurethanes, polyacrylates, and polyvinyl acetate.

19. The regenerable antimicrobial coating of claim 16, wherein the doped polymer is a mixture that further comprises a hydrophilic acrylic polymer.

20. The regenerable antimicrobial coating of claim 16, wherein said coating is a UV-curable coating, water-borne coating, or solvent-borne coating.

21. The regenerable antimicrobial coating of claim 20, wherein said UV-curable coating further comprises a binder; curing agents; stabilizers; an acrylate oligomer; a urethane oligomer, a crosslinking agent such as tris (2-hydroxy ethyl) isocyanurate triacrylate and/or hexane diol diacrylate, a defoamer, a thermal stabilizer, a non-blocking slip additive, a photoinitiator, a near-UV photoinitiator, or mixtures thereof.

22. The regenerable antimicrobial coating of claim 20, wherein said water-borne coating comprises a self-crosslinking linking acrylic dispersion, a UV curable polyurethane dispersion, or a self-crosslinking polyurethane dispersion, and further comprise an alcohol, a glycol, a defoamer, a photoinitiator, a thermal stabilizer, an anti-oxidant, a surfactant, or mixtures thereof.

23. The regenerable antimicrobial coating of claim 20, wherein said solvent-borne coating further comprises a solvent selected from the group of methylethylketone, ethanol, and mixtures thereof; and a coating polymer selected from the group consisting of polyvinyl acetate and polyvinyl acetate-crotonic acid copolymer; and further comprise defoamers, photoinitiators, thermal stabilizers, anti-oxidants, surfactants or mixtures thereof.

* * * * *